(12) United States Patent
Motoki et al.

(10) Patent No.: US 8,501,733 B2
(45) Date of Patent: Aug. 6, 2013

(54) SPIROAMINODIHYDROTHIAZINE DERIVATIVES

(75) Inventors: Takafumi Motoki, Tsukuba (JP); Toshihiko Kaneko, Tokyo (JP); Noboru Yamamoto, Tsukuba (JP); Afzal Khan, London (GB)

(73) Assignee: Eisai R&D Management Co., Ltd., Tokyo (JP)

( * ) Notice: Subject to any disclaimer, the term of this patent is extended or adjusted under 35 U.S.C. 154(b) by 293 days.

(21) Appl. No.: 13/055,830

(22) PCT Filed: Jul. 24, 2009

(86) PCT No.: PCT/JP2009/063627
§ 371 (c)(1),
(2), (4) Date: Jan. 25, 2011

(87) PCT Pub. No.: WO2010/013794
PCT Pub. Date: Feb. 4, 2010

(65) Prior Publication Data
US 2011/0152253 A1 Jun. 23, 2011

Related U.S. Application Data

(60) Provisional application No. 61/084,120, filed on Jul. 28, 2008.

(30) Foreign Application Priority Data

Jul. 28, 2008 (WO) .................. PCT/JP2008/063516

(51) Int. Cl.
*C07D 513/10* (2006.01)
*A61K 31/547* (2006.01)

(52) U.S. Cl.
USPC ............................................ 514/224.5; 544/6

(58) Field of Classification Search
USPC .......................................... 544/6; 514/224.5
See application file for complete search history.

(56) References Cited

U.S. PATENT DOCUMENTS

| | | | |
|---|---|---|---|
| 3,227,713 | A | 1/1966 | Behner et al. |
| 3,235,551 | A | 2/1966 | Werner et al. |
| 7,648,983 | B2 | 1/2010 | Audia et al. |
| 2004/0110743 | A1 | 6/2004 | Miyamato et al. |
| 2006/0052406 | A1 | 3/2006 | Fisher et al. |
| 2007/0021454 | A1 | 1/2007 | Coburn et al. |
| 2008/0139538 | A1 | 6/2008 | McGaughey et al. |
| 2009/0082560 | A1 | 3/2009 | Kobayashi et al. |
| 2009/0209755 | A1 | 8/2009 | Suzuki et al. |
| 2010/0075957 | A1 | 3/2010 | Tamura et al. |
| 2010/0093999 | A1 | 4/2010 | Motoki et al. |
| 2010/0160290 | A1 | 6/2010 | Kobayashi et al. |
| 2010/0317850 | A1 | 12/2010 | Suzuki et al. |
| 2011/0009395 | A1 | 1/2011 | Audia et al. |
| 2011/0207723 | A1 | 8/2011 | Motoki et al. |

FOREIGN PATENT DOCUMENTS

| | | |
|---|---|---|
| EP | 1 942 105 | 7/2008 |
| EP | 2 233 474 | 9/2010 |
| JP | 09-067355 | 3/1997 |
| JP | 2004-149429 | 5/2004 |
| WO | 01/87293 | 11/2001 |
| WO | 02/096897 | 12/2002 |
| WO | 2004/014843 | 2/2004 |
| WO | 2004/043916 | 5/2004 |
| WO | 2005/058311 | 6/2005 |
| WO | 2005/097767 | 10/2005 |
| WO | 2006/041404 | 4/2006 |
| WO | 2006/041405 | 4/2006 |
| WO | WO 2007/011810 | 1/2007 |
| WO | WO 2007/049532 | 5/2007 |
| WO | 2008/133273 | 11/2008 |
| WO | 2008/133274 | 11/2008 |
| WO | WO 2010/013302 | 2/2010 |
| WO | WO 2010/013794 | 2/2010 |
| WO | WO 2011/009897 | 1/2011 |
| WO | WO 2011/009898 | 1/2011 |

OTHER PUBLICATIONS

Kristian et al. Chemical Papers (1999), 53(1), 49-52.*
Response to Office Action from Chinese Application No. 200980101688.X and English Translation (Jun. 15, 2012).
Response to Written Opinion from Singapore Application No. 201102027-8 (Jul. 5, 2012).
Bobrov et al., "Interaction of Quinone Oxide with Thiourea" Chemistry and Chemical Technology 33(10):15-18 (1990) (original and English language translation).
Office Action from U.S. Appl. No. 12/355,154 (Jun. 3, 2011).
Office Action from Japanese Application No. 2009-550050 and English translation (Feb. 9, 2011).
Office Action from Chilean Application No. 96-2009 and English Translation (Dec. 12, 2011).
Response to Office Action from Chilean Application No. 96-2009 and English Translation (Mar. 22, 2012).
Written Opinion from Singapore Application No. 201102027-8 (Mar. 15, 2012).

(Continued)

*Primary Examiner* — Kahsay T Habte
(74) *Attorney, Agent, or Firm* — Fish & Richardson P.C.

(57) ABSTRACT

A compound represented by the general formula (I): or a pharmaceutically acceptable salt thereof, has an Aβ production inhibitory effect or a BACE1 inhibitory effect and is useful as a prophylactic or therapeutic agent for a neurodegenerative disease caused by Aβ and typified by Alzheimer-type dementia.

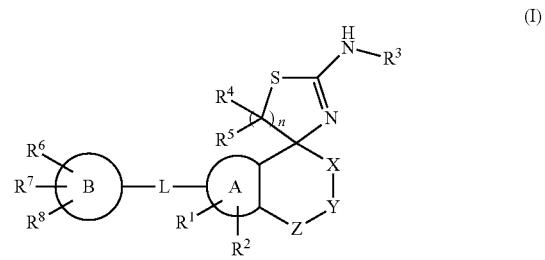

(I)

13 Claims, No Drawings

(56) References Cited

OTHER PUBLICATIONS

Khimiya i Khimicheskava Tekhologiya, 33(10):15-18 (1990).
Meredith et al., "P-Glycoprotein Efflux and Other Factors Limit Brain Amyloid β Reduction by β-Site Amyloid Precursor Protein-Cleaving Enzyme 1 Inhibitors in Mice," *The Journal of Pharmacology and Experimental Therapeutics*, 326(2):502-513 (2008).
Sankaranarayanan et al., "In Vivo β-Secretase 1 Inhibition Leads to Brain Aβ Lowering and Increased α-Secretase Processing of Amyloid Precursor Protein without Effect on Neuregulin-1," *The Journal of Pharmacology and Experimental Therapeutics*, 324(3):957-969 (2008).
Acceptance of Complete Specification from South African Application No. 2010/04799 (Aug. 16, 2011).
Amended Claims and Specification Filed with Response to Office Action from Chilean Application No. 96-2009 and English Translation (Nov. 4, 2011).
Amendment and Response to Office Action from Mexican Application No. MX/a/2010/007337 and English Translation (Jan. 3, 2012).
Amendment and Response to Office Action from Singapore Application No. 201102027-8 (Dec. 28, 2011).
Amendment and Response to Office Action from U.S. Appl. No. 12/568,151 (Dec. 22, 2011).
Argument and Amendment in Response to Office Action from Japanese Application No. 2009-550050 and English Translation (Apr. 12, 2010).
Argument and Amendment in Response to Office Action from New Zealand Application No. 586796 (Apr. 28, 2011).
Argument and Amendment in Response to Office Action from Pakistan Application No. 43/2009 (May 21, 2010).
Decision of Granting Patent from Japanese Application No. 2009-550050 and English Translation (May 7, 2010).
English Translation of Office Action from Mexican Application No. MX/a/2010/007337 (2011).
European Search Report for App. Ser. No. EP 09 81 7719, dated Feb. 14, 2012.
Examination Report and Notice of Acceptance of Complete Specification from New Zealand Application No. 586796 (Oct. 6, 2011).
Extended Search Report from European Application No. 09701914.5 (Sep. 30, 2011).
International Preliminary Report on Patentability from PCT Application No. PCT/JP2009/050511 (Aug. 31, 2010).
International Search Report from PCT Application No. PCT/JP2009/050511 (Mar. 24, 2009).
Newspaper Publication of Venezuelan Application No. 2009-000078 (2011).
Notice of Allowance from U.S. Appl. No. 12/568,151 (Jan. 4, 2012).
Office Action from Chilean Application No. 96-2009 and English Translation (2011).
Office Action from Chilean Application No. 96-2009 and English Translation (Aug. 1, 2011).
Office Action from Mexican Application No. MX/a/2010/007337 and English Translation (Oct. 19, 2011).
Office Action from New Zealand Application No. 586796 (Feb. 21, 2011).
Office Action from Pakistan Application No. 43/2009 (Mar. 26, 2010).
Office Action from U.S. Appl. No. 12/568,151 (Oct. 24, 2011).
Official Acceptance Notice for Pakistan Application No. 43/2009 (Jun. 10, 2010).
Response to Office Action from Chilean Application No. 96-2009 and English Translation (Nov. 4, 2011).
Restriction Requirement from U.S. Appl. No. 12/355,154 (Apr. 19, 2011).
Response to Restriction Requirement from U.S. Appl. No. 12/355,154 (May 9, 2011).
Amendment in Reply to Office Action of Jun. 3, 2011 in U.S. Appl. No. 12/355,154 (Sep. 2, 2011).
Supplemental Amendment in Reply to Office Action of Jun. 3, 2011 in U.S. Appl. No. 12/355,154 (Sep. 27, 2011).
Notice of Allowance from U.S. Appl. No. 12/355,154 (Oct. 5, 2011).
Amendment filed with Request for Continued Examination from U.S. Appl. No. 12/355,154 (Jan. 5, 2012).
Notice of Allowance from U.S. Appl. No. 12/355,154 (Jan. 18, 2012).
Notice of Allowance from U.S. Appl. No. 12/355,154 (Feb. 17, 2012).
Written Opinion from Singapore Application No. 201102027-8 (Aug. 24, 2011).
Cohen, N. and Banner, B., "Synthesis of 2-Amino-5,6-dihydro-4*H*-1,3-thiazines and Related Compounds by Acid Catalyzed Cyclization of Allylic Isothiuronium Salts", Journal of Heterocyclic Chemistry, 14:717-723 (1977).
Forman et al., "Differential Effects of the Swedish Mutant Amyloid Precursor Protein on s-Amyloid Accumulation and Secretion in Neurons and Nonneuronal Cell", The Journal of Biological Chemistry 272 (51):32247-32253 (1997).
Glenner, G. and Wong, C., "Alzheimer's Disease: Initial Report of the Purification and Characterization of a Novel Cerebrovascular Amyloid Protein", Biochemical and Biophysical Research Communications, 120 (3): 885-890 (1984).
Gong et al., "Alzheimer's disease-effected brain. Prsence of oligomeric Aβ ligands (ADDLs) suggests a molecular basis for reversible memory loss", PNAS, USA 100 (18):10417-10422 (2003).
Gouras et al., "Short Communication Intraneuronal Aβ42 Accumulation in Human Brain", American Journal of Pathology, 156(1): 15-20 (2000).
Hock et al., "Antibodies against β-Amyloid Slow Cognitive Decline in Alzheimer's Disease", Neuron, 38:547-554 (2003).
Jarrett et al., "The Carboxy Terminus of the β Amyloid Protein is Critical for the Seeding of Amyloid Formation: Implications for the Pathogenesis of Alzheimer's Disease", Biochemistry, 32 (18): 4693-4697 (1993).
Kuo et al., "A Synthesis of Estrone via Novel Intermediates. Mechanism of the Coupling Reaction of a Vinyl Carbinol with a β Diketone", Journal of Organic Chemistry, 33: 3126-3132 (1968).
Masters et al., "Amyloid plaque core protein in Alzheimer disease and Down Syndrome", PNAS, USA, 82 (12): 4245-4249 (1985).
Scheuner et al., "Secreted amyloid β-protein similar to that in the senile plaques of Alzheimer's disease is increased in vivo by the presenilin 1 and 2 and APP mutations linked to familial Alzheimer's disease", Nature Medicine, 2 (8): 864-870 (1996).
Office Action from Chinese Application No. 200980101688.X and English Translation (Apr. 1, 2012).
Decision of Grant dated Feb. 23, 2012 for Ukraine App. Ser. No. a201010101 and English Translation.
Notice of Acceptance for New Zealand App. Ser. No. 591878, dated May 17, 2012.
Office Action from Canadian App. Ser. No. 2,711,655, dated Jun. 5, 2012.
Office Action from Russian App. Ser. No. 2010134403, dated May 14, 2012 and English Translation.
Office Action from U.S. Appl. No. 13/333,238, dated Jun. 18, 2012.
Examination Report from Chilean App. Ser. No. 702-2-011, dated May 14, 2012 and English Translation.
Examination Report from Australian App. Ser. No. 2009205072, dated Jul. 19, 2012.
Examination Report from GCC App. Ser. No. 12680 and English translation (Sep. 15, 2012).
Examination Report from GCC App. Ser. No. 14375 and English translation (Jul. 18, 2012).
Notification of Examination from Ukraine App. Ser. No. a201010101 and English translation (Aug. 3, 2012).
Response to Communication pursuant to Rules 70(2) and 70a(2) in European App. Ser. No. 09817719.9 (Jul. 26, 2012).
Response to Examiner's report in Chilean App. Ser. No. 702-2011 and English translation (Aug. 8, 2012).
Response to Office Action in Mexican App. Ser. No. MX/a/2011/003189 and English translation (Aug. 28, 2012).
Response to Office Action in Russian App. Ser. No. 2010134403 and English translation (Aug. 14, 2012).
Office Action from Mexican Application No. MX/a/2011/003189 and English Translation (Jun. 25, 2012).

\* cited by examiner

SPIROAMINODIHYDROTHIAZINE DERIVATIVES

TECHNICAL FIELD

The present invention relates to a spiroaminodihydrothiazine derivative and pharmaceutical use thereof. More particularly, the present invention relates to a spiroaminodihydrothiazine derivative which has an amyloid-β (hereinafter referred to as Aβ) protein production inhibitory effect or a beta-site amyloid-β precursor protein cleavage enzyme 1 (hereinafter referred to as BACE1) inhibitory effect and is effective for treating a neurodegenerative disease caused by Aβ protein, in particular, Alzheimer-type dementia, Down's syndrome or the like, and to a pharmaceutical composition comprising the spiroaminodihydrothiazine derivative as an active ingredient.

BACKGROUND ART

Alzheimer's disease is a disease characterized by degeneration and loss of neurons as well as formation of senile plaques and neurofibrillary tangles. Currently, Alzheimer's disease is treated only with symptomatic treatment using a symptom improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as metabolites of amyloid precursor proteins (hereinafter referred to as APP) are highly involved in degeneration and loss of neurons and onset of symptoms of dementia (see Non-Patent Documents 3 and 4, for example). Aβ-proteins have, as main components, Aβ40 consisting of 40 amino acids and Aβ40 with two amino acids added at the C-terminal. The Aβ40 and Aβ42 are known to have high aggregability (see Non-Patent Document 5, for example) and to be main components of senile plaques (see Non-Patent Documents 5, 6 and 7, for example). Further, it is known that the Aβ40 and Aβ42 are increased by mutation in APP and presenilin genes which is observed in familial Alzheimer's disease (see Non-Patent Documents 8, 9 and 10, for example). Accordingly, a compound that reduces production of Aβ40 and Aβ42 is expected as a progression inhibitor or prophylactic agent for Alzheimer's disease.

Aβ is produced by cleaving APP by beta-secretase (BACE1) and subsequently by gamma-secretase. For this reason, attempts have been made to create gamma-secretase and beta-secretase inhibitors in order to inhibit Aβ production. Already known beta-secretase inhibitors are reported in Patent Documents 1 to 15 and Non-Patent Documents 1 and 2 shown below and the like. In particular, Patent Documents 1, 14 and 15 describe an aminodihydrothiazine derivative and a compound having beta-secretase inhibitory activity, that is, BACE1 inhibitory activity.

PRIOR TECHNICAL DOCUMENTS

Patent Documents

[Patent Document 1] WO 2007/049532
[Patent Document 2] U.S. Pat. No. 3,235,551
[Patent Document 3] U.S. Pat. No. 3,227,713
[Patent Document 4] JP-A-09-067355
[Patent Document 5] WO 01/087293
[Patent Document 6] WO 04/014843
[Patent Document 7] JP-A-2004-149429
[Patent Document 8] WO 02/96897
[Patent Document 9] WO 04/043916
[Patent Document 10] WO 2005/058311
[Patent Document 11] WO 2005/097767
[Patent Document 12] WO 2006/041404
[Patent Document 13] WO 2006/041405
[Patent Document 14] WO 2008/133273
[Patent Document 15] WO 2008/133274

Non-Patent Documents

[Non-Patent Document 1] Journal of Heterocyclic Chemistry, Vol. 14, p. 717-723 (1977)
[Non-Patent Document 2] Journal of Organic Chemistry, Vol. 33, p. 3126-3132 (1968)
[Non-Patent Document 3] Klein W L, and seven others, Alzheimer's disease-affected brain: Presence of oligomeric Aβ ligands (ADDLs) suggests a molecular basis for reversible memory loss, Proceedings of National Academy of Science USA 2003, Sep. 2; 100 (18), p. 10417-10422.
[Non-Patent Document 4] Nitsch R M, and sixteen others, Antibodies against β-amyloid slow cognitive decline in Alzheimer's disease, Neuron, 2003, May 22; 38, p. 547-554.
[Non-Patent Document 5] Jarrett J T, and two others, The carboxy terminus of the β amyloid protein is critical for the seeding of amyloid formation: Implications for the pathogenesis of Alzheimers' disease, Biochemistry, 1993, 32 (18), p. 4693-4697.
[Non-Patent Document 6] Glenner G G, and one other, Alzheimer's disease: initial report of the purification and characterization of a novel cerebrovascular amyloid protein, Biochemical and biophysical research communications, 1984, May 16, 120 (3), p. 885-890.
[Non-Patent Document 7] Masters C L, and five others, Amyloid plaque core protein in Alzheimer disease and Down syndrome, Proceedings of National Academy of Science USA, 1985, June, 82 (12), p. 4245-4249.
[Non-Patent Document 8] Gouras G K, and eleven others, Intraneuronal Aβ42 accumulation in human brain, American Journal of Pathology, 2000, January, 156 (1), p. 15-20.
[Non-Patent Document 9] Scheuner D, and twenty others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2 (8), p. 864-870.
[Non-Patent Document 10] Forman M S, and four others, Differential effects of the swedish mutant amyloid precursor protein on β-amyloid accumulation and secretion in neurons and nonneuronal cells, The Journal of Biological Chemistry, 1997, Dec. 19, 272 (51), p. 32247-32253.

SUMMARY OF INVENTION

Problem to be Solved by the Invention

An object of the present invention is to provide a spiroaminodihydrothiazine compound which differs from an aminodihydrothiazine derivative and a compound having BACE1 inhibitory activity described in Patent Document 1 and which has an Aβ production inhibitory effect or a BACE1 inhibitory effect and is useful as a prophylactic or therapeutic agent for a neurodegenerative disease caused by Aβ and typified by Alzheimer-type dementia, and pharmaceutical use thereof.

Means for Solving the Problem

The present invention relates to:
[1] A compound represented by the formula (I):

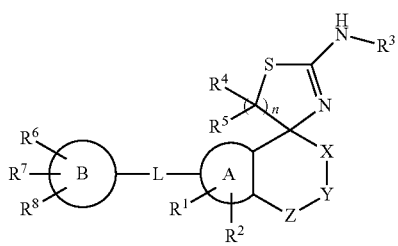

[Formula 1]

or a pharmaceutically acceptable salt thereof, wherein

Ring A is a C6-10 aryl group or a 5- to 10-membered heterocyclic group,

L is a single bond, an oxygen atom or a group represented by the formula —C(=O)NR$^L$— (wherein R$^L$ is a hydrogen atom or a C1-6 alkyl group which may have 1 to 3 substituents selected from Substituent Group α) or a C1-6 alkylene group, a C2-6 alkenylene group or a C2-6 alkynylene group which may have 1 to 3 substituents selected from Substituent Group α, respectively, Ring B is a C3-8 cycloalkyl group, a C6-10 aryl group or a 5- to 10-membered heterocyclic group, X is a C1-3 alkylene group or a C2-3 alkenylene group which may have 1 to 3 substituents selected from Substituent Group α, respectively, Y is an oxygen atom, a sulfur atom, a sulfoxide group, a sulfone group or a group represented by the formula —NR$^Y$— (wherein R$^Y$ is a hydrogen atom or a C1-6 alkyl group, a C1-6 alkylcarbonyl group, a C3-8 cycloalkylcarbonyl group, a C6-10 arylcarbonyl group, a C1-6 alkylsulfonyl group, a C6-10 arylsulfonyl group, a C6-10 aryl group or a 5- to 6-membered heteroaryl group which may have 1 to 3 substituents selected from Substituent Group α, respectively), Z is a single bond or a C1-3 alkylene group, R$^1$ and R$^2$ are each independently a hydrogen atom, a halogen atom, a hydroxy group or a cyano group, or a C1-6 alkyl group or a C1-6 alkoxy group which may have 1 to 3 substituents selected from Substituent Group α, respectively, R$^3$ is a hydrogen atom or a C1-6 alkyl group, a C1-6 alkylcarbonyl group, a C6-10 arylcarbonyl group, a C1-6 alkylsulfonyl group, a C6-10 arylsulfonyl group, a C3-8 cycloalkyl group, a C6-10 aryl group or a 5- to 10-membered heterocyclic group which may have 1 to 3 substituents selected from Substituent Group α, respectively, R$^4$ and R$^5$ are each independently a hydrogen atom, a halogen atom or a hydroxy group, or a C1-6 alkyl group, a C1-6 alkyloxy group, a C3-8 cycloalkyl group, a C3-8 cycloalkyloxy group, a C6-10 aryl group or a 5- to 10-membered heterocyclic group which may have 1 to 3 substituents selected from Substituent Group α, respectively, R$^6$, R$^7$ and R$^8$ are each independently a hydrogen atom, a halogen atom, a hydroxy group or a cyano group, or a C1-6 alkyl group, a C2-6 alkenyl group, a C2-6 alkynyl group, a C1-6 alkoxy group, a C3-8 cycloalkyl group, a C3-8 cycloalkyloxy group, a C6-10 aryl group or a 5- to 10-membered heterocyclic group which may have 1 to 3 substituents selected from Substituent Group α, respectively, and n is an integer of 1 to 3

[Substituent Group α: a hydrogen atom, a halogen atom, a hydroxy group, an oxo group, a cyano group, a C1-6 alkyl group, a trifluoromethyl group, a trifluoromethoxy group, a C1-6 alkoxy group, a C3-8 cycloalkyl group, a C3-8 cycloalkyloxy group, a C6-10 aryl group and a 5- to 10-membered heterocyclic group];

[2] The compound or pharmaceutically acceptable salt thereof according to [1] above, wherein X is a C1-3 alkylene group which may have 1 to 3 substituents selected from Substituent Group α;

[3] The compound or pharmaceutically acceptable salt thereof according to [1] or [2] above, wherein Y is an oxygen atom;

[4] The compound or pharmaceutically acceptable salt thereof according to [1] or [2] above, wherein Y is a sulfur atom or a sulfone group;

[5] The compound or pharmaceutically acceptable salt thereof according to [1] or [2] above, wherein Y is a group represented by the formula —NR$^Y$— (wherein R$^Y$ is a hydrogen atom or a C1-6 alkyl group, a C1-6 alkylcarbonyl group, a C3-8 cycloalkylcarbonyl group, a C6-10 arylcarbonyl group, a C1-6 alkylsulfonyl group, a C6-10 arylsulfonyl group, a C6-10 aryl group or a 5- to 6-membered heteroaryl group which may have 1 to 3 substituents selected from Substituent Group α, respectively);

[6] The compound or pharmaceutically acceptable salt thereof according to any one of [1] to [5] above, wherein L is a group represented by the formula —C(=O)NR$^L$— (wherein R$^L$ is a hydrogen atom or a C1-6 alkyl group which may have 1 to 3 substituents selected from Substituent Group α);

[7] The compound or pharmaceutically acceptable salt thereof or solvate thereof according to any one of claims 1 to 6, wherein the compound is selected from the following compounds:

1) (−)—N-(2'-amino-2,3,5',6'-tetrahydrospiro[chromene-4, 4'-[1,3]thiazin]-6-yl)-5-cyanopyridine-2-carboxamide,
2) N-(2'-amino-2,3,5',6'-tetrahydrospiro[chromene-4,4'-[1, 3]thiazin]-6-yl)-5-trifluoromethylpyridine-2-carboxamide,
3) N-(2'-amino-2,3,5',6'-tetrahydrospiro[chromene-4,4'-[1, 3]thiazin]-6-yl)-3,5-difluoropyridine-2-carboxamide,
4) N-(2'-amino-2,3,5',6'-tetrahydrospiro[chromene-4,4'-[1, 3]thiazin]-6-yl)-5-bromopyrimidine-2-carboxamide,
5) N-(2'-amino-2,3,5',6'-tetrahydrospiro[chromene-4,4'-[1, 3]thiazin]-6-yl)-5-bromopyrimidine-2-carboxamide and
6) N-(2'-amino-2,3,5',6'-tetrahydrospiro[chromene-4,4'-[1, 3]thiazin]-6-yl)-3,5-dichloropyridine-2-carboxamide;

[8] A pharmaceutical composition comprising the compound or pharmaceutically acceptable salt thereof according to any one of [1] to [7] above as an active ingredient;

[9] The pharmaceutical composition according to [8] above for inhibiting production of amyloid-β protein;

[10] The pharmaceutical composition according to [8] above for inhibiting beta-site amyloid-β precursor protein cleaving enzyme 1 (BACE1);

[11] The pharmaceutical composition according to any one of [8] to [10] above for treating a neurodegenerative disease; and

[12] The pharmaceutical composition according to [11] above, wherein the neurodegenerative disease is Alzheimer-type dementia or Down's syndrome.

Meanings of symbols, terms and the like used in the present specification will be explained and the present invention will be described in detail below.

In the present specification, a structural formula of a compound may represent a certain isomer for convenience. However, the present invention includes all isomers and isomer mixtures such as geometric isomers which can be generated from the structure of a compound, optical isomers based on asymmetric carbon, stereoisomers and tautomers. The present invention is not limited to the description of a chemical formula for convenience and may include any one of the isomers or mixtures thereof. Accordingly, the compound of the present invention may have an asymmetric carbon atom in the molecule and exist as an optically active compound or racemate, and the present invention includes each of the optically active compound and the racemate without limitations. Although crystal polymorphs of the compound may be present, the compound is similarly not limited thereto and may be present as a single crystal form or a mixture of single crystal forms. The compound may be an anhydride or a hydrate. Any of these forms is included in the claims of the present application.

The "halogen atom" herein refers to a fluorine atom, a chlorine atom, a bromine atom, an iodine atom or the like and is preferably a fluorine atom or a chlorine atom.

The "C1-6 alkyl group" refers to an alkyl group having 1 to 6 carbon atoms. Preferable examples of the group include linear or branched alkyl groups such as a methyl group, an ethyl group, an n-propyl group, an isopropyl group, an n-butyl group, an isobutyl group, a t-butyl group, an n-pentyl group, an isopentyl group, a neopentyl group, an n-hexyl group, a 1-methylpropyl group, an 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group and a 3-methylpentyl group. The group is more preferably a methyl group, an ethyl group or an n-propyl group.

The "C2-6 alkenyl group" refers to an alkenyl group having 2 to 6 carbon atoms. Preferable examples of the group include linear or branched alkenyl groups such as a vinyl group, an allyl group, a 1-propenyl group, an isopropenyl group, a 1-buten-1-yl group, a 1-buten-2-yl group, a 1-buten-3-yl group, a 2-buten-1-yl group and a 2-buten-2-yl group.

The "C2-6 alkynyl group" refers to an alkynyl group having 2 to 6 carbon atoms. Preferable examples of the group include linear or branched alkynyl groups such as an ethynyl group, a 1-propynyl group, a 2-propynyl group, a butynyl group, a pentynyl group and a hexynyl group.

The "C1-6 alkylene group" refers to a divalent group derived by excluding any one hydrogen atom from the "C1-6 alkyl group" as defined above. Examples of the group include a methylene group, a 1,2-ethylene group, a 1,1-ethylene group, a 1,3-propylene group, a tetramethylene group, a pentamethylene group and a hexamethylene group.

The "C2-6 alkenylene group" refers to a divalent group derived by excluding any one hydrogen atom from the "C2-6 alkenyl group" as defined above. Examples of the group include a 1,2-vinylene group (ethenylene group), a propenylene group, a butenylene group, a pentenylene group and a hexenylene group.

The "C2-6 alkynylene group" refers to a divalent group derived by excluding any one hydrogen atom from the "C2-6 alkynyl group" as defined above. Examples of the group include an ethynylene group, a propynylene group, a butynylene group, a pentynylene group and a hexynylene group.

The "C1-6 alkyloxy group" refers to an alkyl group having 1 to 6 carbon atoms in which one hydrogen atom is replaced by an oxygen atom. Examples of the group include a methoxy group, an ethoxy group, an n-propoxy group, an isopropoxy group, an n-butoxy group, an isobutoxy group, a sec-butoxy group, a t-butoxy group, an n-pentoxy group, an isopentoxy group, a sec-pentoxy group, a t-pentoxy group, an n-hexoxy group, an isohexoxy group, a 1,2-dimethylpropoxy group, a 2-ethylpropoxy group, a 1-methyl-2-ethylpropoxy group, a 1-ethyl-2-methylpropoxy group, a 1,1,2-trimethylpropoxy group, a 1,1,2-trimethylpropoxy group, a 1,1-dimethylbutoxy group, a 2,2-dimethylbutoxy group, a 2-ethylbutoxy group, a 1,3-dimethylbutoxy group, a 2-methylpentoxy group, a 3-methylpentoxy group and a hexyloxy group.

The "C1-6 alkylsulfonyl group" refers to an alkyl group having 1 to 6 carbon atoms in which one hydrogen atom is replaced by a sulfonyl group. Examples of the group include a methylsulfonyl group, an ethylsulfonyl group, an n-propylsulfonyl group, an isopropylsulfonyl group, an n-butylsulfonyl group, an isobutylsulfonyl group, a t-butylsulfonyl group, an n-pentylsulfonyl group, an isopentylsulfonyl group, a neopentylsulfonyl group, an n-hexylsulfonyl group and a 1-methylpropylsulfonyl group.

The "C1-6 alkylcarbonyl group" refers to an alkyl group having 1 to 6 carbon atoms in which one hydrogen atom is replaced by a carbonyl group. Preferable examples of the group include an acetyl group, a propionyl group and a butyryl group.

The "C6-10 aryl group" refers to an aromatic hydrocarbon ring group having 6 to 10 carbon atoms. Examples of the group include a phenyl group and a naphthyl group. A phenyl group is particularly preferable.

The "C6-10 arylcarbonyl group" refers to a group in which a carbonyl group is bonded to an aromatic hydrocarbon ring group having 6 to 10 carbon atoms. Preferable examples of the group include a benzoyl group and a naphthoyl group. A benzoyl group is more preferable.

The "C6-10 arylsulfonyl group" refers to a group in which a sulfonyl group is bonded to an aromatic hydrocarbon ring group having 6 to 10 carbon atoms. Preferable examples of the group include a benzylsulfonyl group and a naphthylsulfonyl group. A benzylsulfonyl group is more preferable.

The "C3-8 cycloalkyl group" refers to a cyclic alkyl group having 3 to 8 carbon atoms. Preferable examples of the group include a cyclopropyl group, a cyclobutyl group, a cyclopentyl group, a cyclohexyl group, a cycloheptyl group and a cyclooctyl group.

The "C3-8 cycloalkyloxy group" refers to a cyclic alkyl group having 3 to 8 carbon atoms in which one hydrogen atom is replaced by an oxygen atom. Examples of the group include a cyclopropoxy group, a cyclobutoxy group, a cyclopentoxy group, a cyclohexoxy group, a cycloheptyloxy group and a cyclooctyloxy group.

The "C3-8 cycloalkylcarbonyl group" refers to a cyclic alkyl group having 3 to 8 carbon atoms in which one hydrogen atom is replaced by a carbonyl group. Examples of the group include a cyclopropylcarbonyl group, a cyclobutylcarbonyl group, a cyclopentylcarbonyl group, a cyclohexylcarbonyl group, a cycloheptylcarbonyl group and a cyclooctylcarbonyl group.

The "5- to 10-membered heterocyclic group" refers to a heteroatom-containing cyclic group having 5 to 10 members in total. Preferable examples of the group include a piperidinyl group, a pyrrolidinyl group, an azepinyl group, an azocanyl group, a piperazinyl group, a 1,4-diazepanyl group, a morpholinyl group, a thiomorpholinyl group, a pyrrolyl group, an imidazolyl group, a pyrazolyl group, a pyridinyl group, a pyridazinyl group, a pyrimidinyl group, a pyrazinyl group, a triazolyl group, a triazinyl group, a tetrazolyl group, an isoxazolyl group, an oxazolyl group, an oxadiazolyl group, an isothiazolyl group, a thiazolyl group, a thiadiazolyl group, a furyl group, a thienyl group, a quinolinyl group, an isoquinolinyl group, a benzofuryl group, a benzopyranyl group, a benzimidazolyl group, a benzotriazolyl group, a benzoisothiazolyl group, an indolinyl group, an isoindolinyl group, a chromanyl group, an isochromanyl group, a 1,3-dioxaindanyl group and a 1,4-dioxatetralinyl group.

The "5- to 6-membered heteroaryl group" refers to the "5- to 10-membered heterocyclic group" which is a heteroatom-containing aromatic cyclic group having 5 to 6 members in total. Examples of the group include a pyrrolyl group, an imidazolyl group, a pyrazolyl group, a pyridinyl group, a pyridazinyl group, a pyrimidinyl group, a pyrazinyl group, a triazolyl group, a triazinyl group, a tetrazolyl group, an isoxazolyl group, an oxazolyl group, an oxadiazolyl group, an isothiazolyl group, a thiazolyl group, a thiadiazolyl group, a furyl group and a thienyl group.

Examples of the "C1-3 alkylene group" include a methylene group, an ethylene group and a propylene group.

Examples of the "C2-3 alkenylene group" include a vinylene group and a propenylene group.

"Substituent Group α" refers to a hydrogen atom, a halogen atom, a hydroxy group, an oxo group, a cyano group, a C1-6 alkyl group, a trifluoromethyl group, a trifluoromethoxy group, a C1-6 alkoxy group, a C3-8 cycloalkyl group, a C3-8 cycloalkyloxy group, a C6-10 aryl group and a 5- to 10-membered heterocyclic group.

The spiroaminodihydrothiazine derivative of the formula (I) according to the present invention may be a pharmaceutically acceptable salt. Specific examples of the pharmaceutically acceptable salt include inorganic acid salts (such as sulfates, nitrates, perchlorates, phosphates, carbonates, bicarbonates, hydrofluorides, hydrochlorides, hydrobromides and hydroiodides), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

The spiroaminodihydrothiazine derivative of the formula (I) or pharmaceutically acceptable salt according to the present invention may be a solvate thereof. Examples of the solvate include a hydrate. The compound (I) is not limited to a specific isomer and includes all possible isomers (such as a keto-enol isomer, an imine-enamine isomer, a diastereoisomer, an optical isomer and a rotamer) and racemates. For example, the compound (I) includes the following tautomers.

The spiroaminodihydrothiazine derivative is also preferably a compound of the formula (I), wherein L is a group represented by the formula —C(=O)NR$^L$— (wherein R$^L$ is as defined above).

The spiroaminodihydrothiazine derivative is particularly preferably a compound of the formula (I), wherein Y is an oxygen atom and Z is a single bond; wherein Y is an oxygen atom and Z is a C1-3 alkylene which may have 1 to 3 substituents selected from Substituent Group α; or wherein Y is a sulfur atom or a sulfone and Z is a single bond.

Preferable compounds in the present invention include the following compounds:

1) (–)—N-(2'-amino-2,3,5',6'-tetrahydrospiro[chromene-4,4'-[1,3]thiazin]-6-yl)-5-cyanopyridine-2-carboxamide,
2) N-(2'-amino-2,3,5',6'-tetrahydrospiro[chromene-4,4'-[1,3]thiazin]-6-yl)-5-trifluoromethylpyridine-2-carboxamide,
3) N-(2'-amino-2,3,5',6'-tetrahydrospiro[chromene-4,4'-[1,3]thiazin]-6-yl)-3,5-difluoropyridine-2-carboxamide,
4) N-(2'-amino-2,3,5',6'-tetrahydrospiro[chromene-4,4'-[1,3]thiazin]-6-yl)-5-fluoropyridine-2-carboxamide,
5) N-(2'-amino-2,3,5',6'-tetrahydrospiro[chromene-4,4'-[1,3]thiazin]-6-yl)-5-bromopyrimidine-2-carboxamide,
6) N-(2'-amino-2,3,5',6'-tetrahydrospiro[chromene-4,4'-[1,3]thiazin]-6-yl)-5-bromopyridine-2-carboxamide,
7) N-(2'-amino-2,3,5',6'-tetrahydrospiro[chromene-4,4'-[1,3]thiazin]-6-yl)-5-methoxypyrazine-2-carboxamide,
8) N-(2'-amino-2,3,5',6'-tetrahydrospiro[chromene-4,4'-[1,3]thiazin]-6-yl)-3,5-dichloropyridine-2-carboxamide,
9) N-(2'-amino-2,3,5',6'-tetrahydrospiro[chromene-4,4'-[1,3]thiazin]-6-yl)-3-fluoropyridine-2-carboxamide,
10) 6-(5-methoxypyridin-3-yl)-2,3,5',6'-tetrahydrospiro[chromene-4,4'-[1,3]thiazin]-2'-amine,
11) 6-(3,5-dichlorophenyl)-2,3,5',6'-tetrahydrospiro[chromene-4,4'-[1,3]thiazin]-2'-amine,
12) 6-(1-methyl-1H-pyrazol-4-yl)-2,3,5',6'-tetrahydrospiro[chromene-4,4'-[1,3]thiazin]-2'-amine,
13) 6-(2-fluoropyridin-3-yl)-2,3,5',6'-tetrahydrospiro[chromene-4,4'-[1,3]thiazin]-2'-amine,
14) 6-[(2-aminopyridin-3-yl)ethynyl]-2,3,5',6'-tetrahydrospiro[chromene-4,4'-[1,3]thiazin]-2'-amine and
15) 7-fluoro-6-(2-fluoropyridin-3-yl)-2,3,5',6'-tetrahydrospiro[chromene-4,4'-[1,3]thiazin]-2'-amine.

[Formula 2]

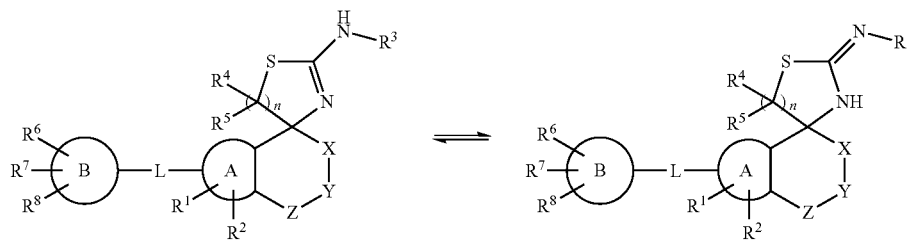

The spiroaminodihydrothiazine derivative of the formula (I) according to the present invention is preferably a compound of the formula (I), wherein X is a C1-3 alkylene group which may have 1 to 3 substituents selected from Substituent Group α, in particular, a methylene or ethylene which may have 1 to 3 substituents selected from Substituent Group α.

The spiroaminodihydrothiazine derivative is also preferably a compound of the formula (I), wherein Y is an oxygen atom, a sulfur atom, a sulfone group or a group represented by the formula —NR$^Y$— (wherein R$^Y$ is as defined above).

More preferable compounds include the following compounds:

1) (–)—N-(2'-amino-2,3,5',6'-tetrahydrospiro[chromene-4,4'-[1,3]thiazin]-6-yl)-5-cyanopyridine-2-carboxamide,
2) N-(2'-amino-2,3,5',6'-tetrahydrospiro[chromene-4,4'-[1,3]thiazin]-6-yl)-5-trifluoromethylpyridine-2-carboxamide,
3) N-(2'-amino-2,3,5',6'-tetrahydrospiro[chromene-4,4'-[1,3]thiazin]-6-yl)-3,5-difluoropyridine-2-carboxamide, 4) N-(2'-amino-2,3,5',6'-tetrahydrospiro[chromene-4,4'-[1,3]thiazin]-6-yl)-5-bromopyrimidine-2-carboxamide,
5) N-(2'-amino-2,3,5',6'-tetrahydrospiro[chromene-4,4'-[1,3]thiazin]-6-yl)-5-bromopyrimidine-2-carboxamide and
6) N-(2'-amino-2,3,5',6'-tetrahydrospiro[chromene-4,4'-[1,3]thiazin]-6-yl)-3,5-dichloropyridine-2-carboxamide.

Next, methods for preparing the compound of the formula (I) [hereinafter referred to as compound (I); a compound represented by another formula is similarly described] or pharmaceutically acceptable salt thereof according to the present invention will be described.

The later-described "leaving group" in the raw material compound used in preparation of the compound of the formula (I) according to the present invention may be any leaving group used for nucleophilic substitution reaction. Preferable examples of the leaving group include a halogen atom; a C1-6 alkylsulfonyloxy group which may be substituted with 1 to 3 substituents selected from the above-described Substituent Group α; a C1-6 alkylcarbonyloxy group which may be substituted with 1 to 3 substituents selected from the above-described Substituent Group α; and an arylsulfonyloxy group which may be substituted with 1 to 3 substituents selected from the above-described Substituent Group α. Specific examples of the leaving group include a chlorine atom, a bromine atom, an iodine atom, a methanesulfonyloxy group, a trifluorocarbonyloxy group, a trifluoromethanesulfonyloxy group and a p-toluenesulfonyloxy group.

General Preparation Method 1:

[Formula 3]

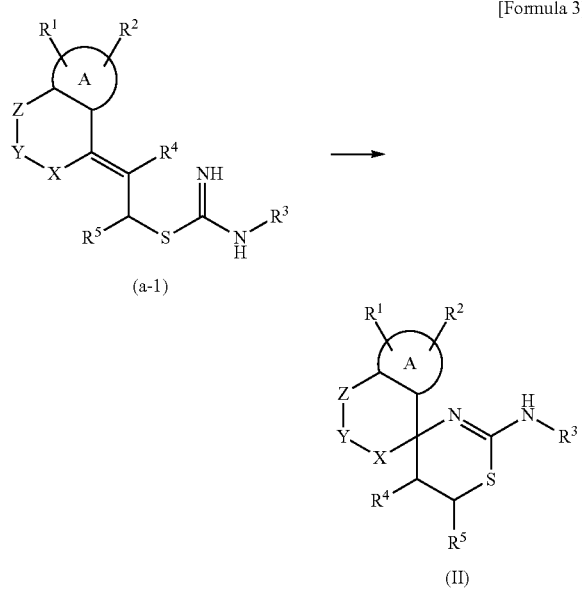

In the formula, Ring A, $R^1$, $R^2$, $R^3$, $R^4$, $R^5$, X, Y and Z are as defined above.

This step is a method of obtaining a compound (II) by cyclizing a compound (a-1) with an acid.

This reaction is not particularly limited insofar as it does not inhibit the reaction and allows the starting material to be dissolved therein to a certain extent. For example, the reaction can be performed by causing one equivalent to a large excess of an appropriate acid to act on the compound (a-1) in the presence or absence of a solvent such as benzene, toluene or dichloromethane. Further, an acid may also be used as a solvent. Examples of the acid used include sulfuric acid, trifluoroacetic acid, methanesulfonic acid, trifluoromethanesulfonic acid and mixtures thereof. The reaction time is not particularly limited and is usually 1 to 72 hours, and preferably 1 to 48 hours. The reaction temperature is usually ice-cold temperature to solvent reflux temperature.

Method for synthesizing compound (II)

The compound (a-1) used in General Preparation Method 1 can be synthesized from a compound (a-2) by Method 1 or Method 2.

Method 1:

[Formula 4]

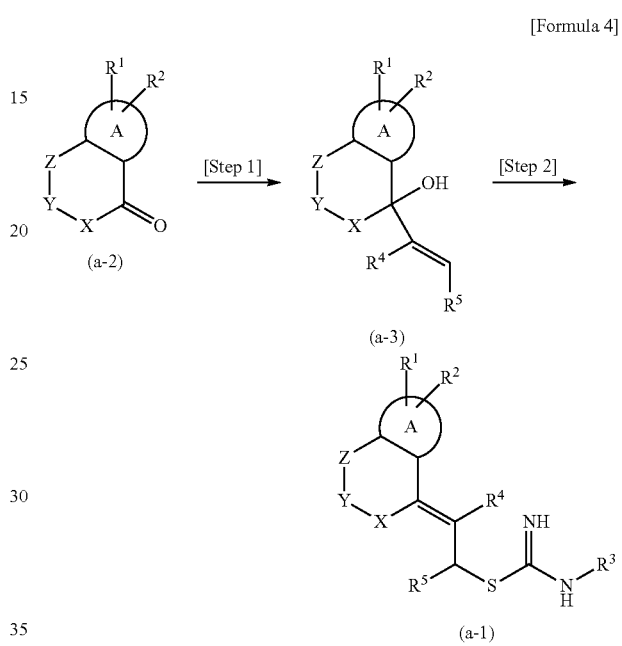

In the formula, each symbol represents the same meaning as described above.

Method 1 is a method of preparing the compound (a-1) from the compound (a-2) as a starting material in two steps. The compound (a-2) can be a commercially available product used as is, can also be prepared from a commercially available product by a known method, and can further be prepared by a method described in Preparation Examples among Examples.

Step 1:

This step is a step of obtaining a compound (a-3) by addition reaction of a vinyllithium reagent or a vinyl Grignard reagent, which is commercially available or can be prepared by a known method, with the compound (a-2). This reaction can be performed under the same conditions as those described in J. Am. Chem. Soc. 2006, 128, 9998-9999 and J. Heterocyclic Chem. 1982, 19, 1041-1044, for example. The solvent used in the reaction varies according to the starting material and the reagent used, and is not particularly limited insofar as it does not inhibit the reaction, allows the starting material to be dissolved therein to a certain extent, and is always inert during the reaction. Preferable examples of the solvent include organic solvents such as diethyl ether, tetrahydrofuran, 1,4-dioxane, 1,2-dimethoxyethane, benzene and toluene, and mixed solvents thereof. The reaction time is not particularly limited and is usually 0.1 to 48 hours, and preferably 0.1 to 12 hours. The reaction temperature varies according to the starting material, the reagent used and the like, and is preferably maintained to be low, for example, at −78° C. to room temperature to minimize formation of a by-product.

Favorable results such as an improved yield and a reduced reaction time may be achieved by addition of a Lewis acid such as zinc chloride, or TMEDA (tetramethylethylenediamine) or HMPA (hexamethylphosphoramide) as an additive, for example.

Step 2:

This step is a step of obtaining the compound (a-1) by reacting the compound (a-3) with thiourea or N-substituted thiourea in the presence of an acid.

The reaction in this step can be performed under the same conditions as those described in Russ. J. Org. Chem., 2006, 42 (1), 42-47, for example.

Examples of the acid used in this reaction include acetic acid, trifluoroacetic acid, hydrogen chloride, sulfuric acid and mixtures thereof. The reaction can be performed by causing one or more equivalents of a thiourea derivative to act on the compound (a-3) in the absence of a solvent or in an organic solvent such as toluene. The reaction time is not particularly limited and is usually 5 minutes to 24 hours, and preferably 5 minutes to 12 hours. The reaction temperature is usually 0° C. to 150° C., and more preferably 0° C. to 100° C.

Method 2:

[Formula 5]

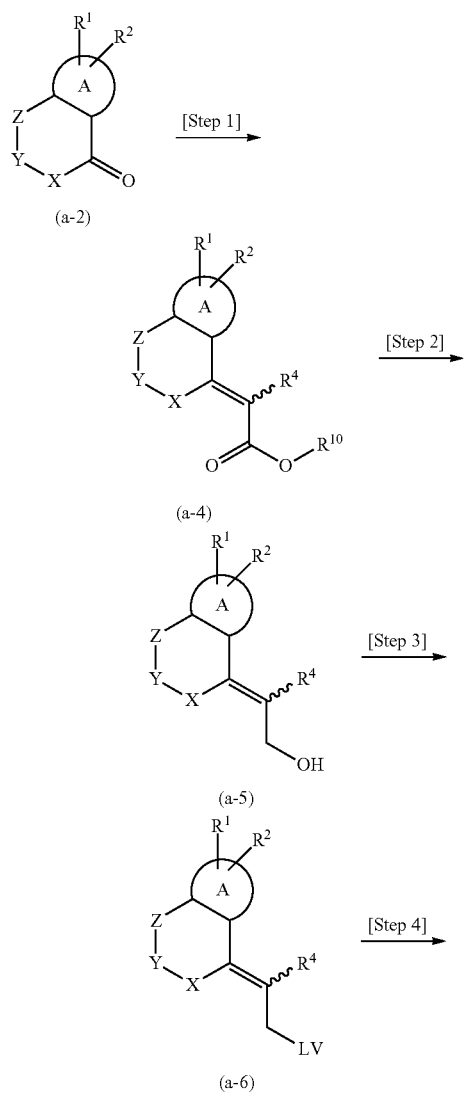

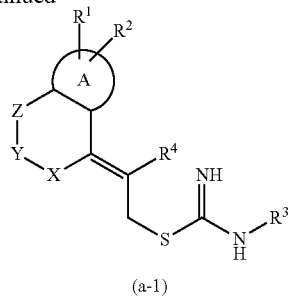

In the formula, Ring A, $R^1$, $R^2$, $R^3$, $R^4$, X, Y and Z are as defined above, LV represents a leaving group and $R^{10}$ represents a C1-6 alkyl group.

Method 2 is a method of preparing the compound (a-1) from the compound (a-2) as a starting material in four steps.

Step 1:

This step is a step of obtaining a compound (a-4) by addition reaction of a Peterson reagent or a Horner-Wadsworth-Emmons reagent with the compound (a-2) under the same conditions as in a known method.

The Peterson reagent or the Horner-Wadsworth-Emmons reagent can be a commercially available product used directly or can be prepared by a method known to a person skilled in the art. Specifically, such a reagent can be prepared by reacting an alkyl trialkylsilylacetate compound or a trialkyl phosphonoacetate compound with a commercially available organometallic reagent, for example, an alkyllithium reagent such as butyllithium, or with an alkoxypotassium or alkoxysodium reagent such as tert-butoxypotassium, or with a corresponding lithium alkylamide reagent or magnesium alkylamide reagent by proton-metal exchange using metallic magnesium or metallic lithium, for example.

The solvent used in this step varies according to the starting material and the reagent used, and is not particularly limited insofar as it does not inhibit the reaction, allows the starting material to be dissolved therein to a certain extent, and is always inert during the reaction. Preferable examples of the solvent include organic solvents such as diethyl ether, tetrahydrofuran, 1,4-dioxane, 1,2-dimethoxyethane, benzene, toluene, methanol and ethanol, and mixed solvents thereof. The reaction time is not particularly limited and is usually 0.1 to 48 hours, and preferably 0.1 to 12 hours. The reaction temperature varies according to the starting material, the reagent used and the like, and is preferably maintained to be low, for example, at −78° C. to room temperature to minimize formation of a by-product.

Step 2:

This step is a step of obtaining an alcohol compound (a-5) by subjecting the ester compound (a-4) to reduction reaction.

Examples of the reducing agent used in the reaction include lithium aluminum hydride, lithium borohydride and diisobutylaluminum hydride. The reaction temperature is not particularly limited and is usually −78° C. to solvent reflux temperature, and preferably −78° C. to room temperature. The solvent used in the reaction is not particularly limited insofar as it does not inhibit the reaction and allows the starting material to be dissolved therein to a certain extent. Preferable examples of the solvent include tetrahydrofuran, diethyl ether, toluene and dichloromethane.

Step 3:

This step is a step of obtaining a compound (a-6) by converting the hydroxyl group of the compound (a-5) to a leaving group.

Examples of the leaving group include the above-described leaving groups. The reaction can be performed under the same conditions as those usually used in reaction of converting a hydroxyl group to such a leaving group. When the leaving group is a halogen atom, for example, the compound (a-6) can be prepared by reacting the compound (a-5) with hydrochloric acid, hydrobromic acid, thionyl chloride, thionyl bromide, phosphorus tribromide or tetrahalogenomethane-triphenylphosphine, for example. The solvent used in the reaction is not particularly limited insofar as it does not inhibit the reaction and allows the starting material to be dissolved therein to a certain extent. Preferable examples of the solvent include benzene, toluene, xylene, dichloromethane and chloroform. The reaction temperature is usually −78° C. to solvent reflux temperature, and preferably ice-cold temperature to solvent reflux temperature. The reaction time is not particularly limited and is usually 5 minutes to 48 hours, and preferably 5 minutes to 12 hours.

When the leaving group is a C1-6 alkylcarbonyloxy group, the compound (a-6) can be prepared by reacting the compound (a-5) with trifluoroacetyl chloride or trifluoroacetic anhydride, for example.

When the leaving group is a C1-6 alkylsulfonyloxy group or an arylsulfonyloxy group, the compound (a-6) can be prepared by reacting the compound (a-5) with methanesulfonyl chloride, p-toluenesulfonyl chloride or trifluoromethanesulfonic anhydride, for example.

The solvent used in the reaction is not particularly limited insofar as it does not inhibit the reaction and allows the starting material to be dissolved therein to a certain extent. Preferable examples of the solvent include tetrahydrofuran, toluene, xylene, dichloromethane, chloroform and N,N-dimethylformamide. The reaction temperature is usually −78° C. to solvent reflux temperature, and preferably −78° C. to room temperature. A favorable result such as an improved yield may be achieved by addition of a base. The base used is not particularly limited insofar as it does not inhibit the reaction. Preferable examples of the base include sodium carbonate, potassium carbonate, triethylamine, pyridine and diisopropylethylamine.

Step 4:

This step is a step of obtaining the compound (a-1) by reacting the compound (a-6) with thiourea or N-substituted thiourea.

Specifically, this reaction can be performed by causing one or more equivalents of thiourea or N-methylthiourea to act on the compound (a-6) in an organic solvent such as methanol, ethanol, 1-propanol, 2-propanol, 1-butanol, tetrahydrofuran, 1,4-dioxane or N,N-dimethylformamide or in an inorganic acid such as hydrobromic acid, for example. The reaction time is not particularly limited and is usually 5 minutes to 24 hours, and preferably 5 minutes to 12 hours. The reaction temperature is usually 0° C. to 150° C., and more preferably room temperature to 100° C.

2. General Preparation Method 2:

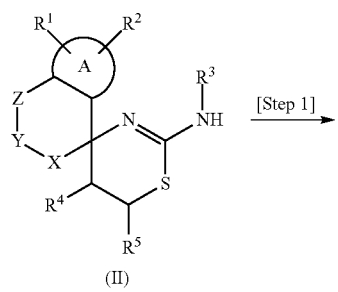

(II)

[Formula 6]

[Step 1]

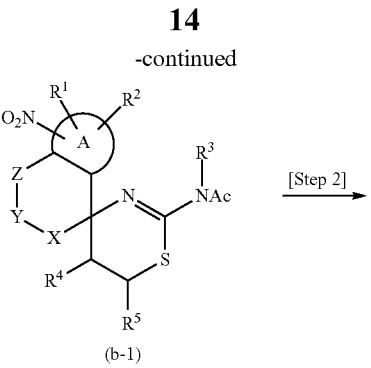

(b-1)

[Step 2]

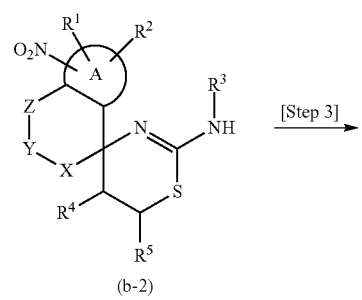

(b-2)

[Step 3]

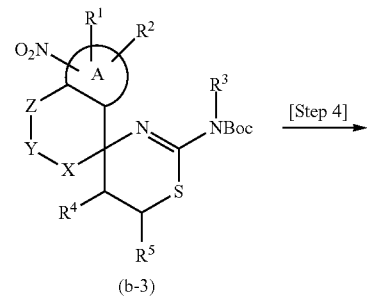

(b-3)

[Step 4]

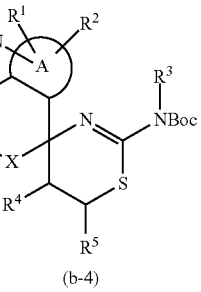

(b-4)

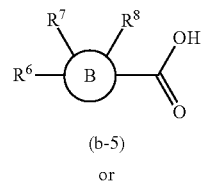

(b-5)

or

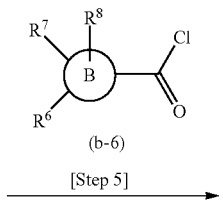

(b-6)

[Step 5]

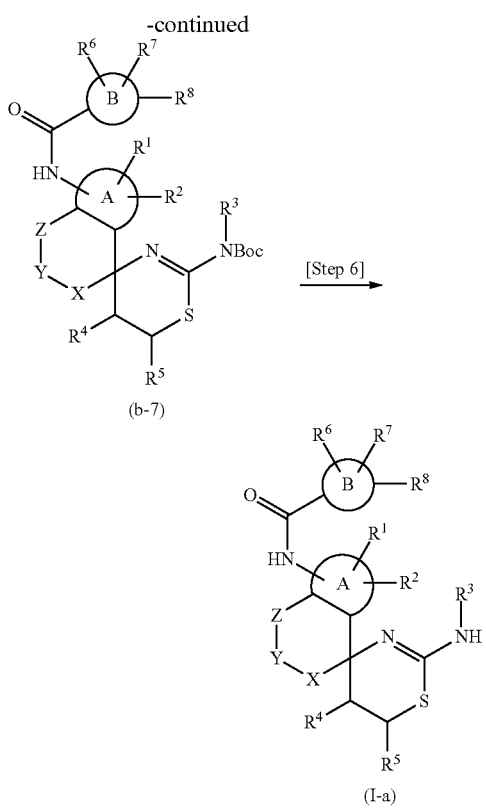

In the formula, Ring A, Ring B, $R^1$, $R^2$, $R^3$, $R^4$, $R^5$, $R^6$, $R^7$, $R^8$, X, Y and Z are as defined above.

General Preparation Method 2 is a method for preparing the compound of the general formula (I) according to the present invention, wherein L is —NHCO—, from the compound (II) obtained in General Preparation Method 1 in six steps.

The compound (II) can be prepared from a commercially available product by the above General Preparation Method 1, and can also be prepared by a method described in Preparation Examples among Examples. Compounds (b-5) and (b-6) each can be a commercially available product used as is, can also be prepared from a commercially available product by a method known to a person skilled in the art, and can further be prepared by a method described in Preparation Examples Among Examples.

Step 1:

This step is a step of preparing a compound (b-1) from the compound (II).

This reaction can be performed by the following known Method 1 or Method 2.

Method 1: Method of Simultaneously Performing Acetylation and Nitration Reactions for Compound (II) in System This reaction can be performed by a method known to a person skilled in the art. Examples of the conditions used in the reaction include concentrated nitric acid/acetic anhydride and fuming nitric acid/acetic anhydride. The reaction temperature is not particularly limited and is usually −20° C. to 50° C., and preferably −20° C. to room temperature.

Method 2: Method of Isolating Acetylated Compound of Compound (II) and then Performing Nitration Step 2-1: This step is a step of obtaining a corresponding acetyl compound by acetylation reaction of the compound (II). The reaction can be performed under the same conditions as those generally used in acetylation of an amino compound such as the conditions described in a document such as T. W. Green and P. G. M. Wuts, "Protective Groups in Organic Chemistry, Second Edition", John Wiley & Sons (1991), p. 351-352. Examples of the acetylating agent used in the reaction include acetyl chloride and acetic anhydride. The reaction temperature is not particularly limited and is usually −20° C. to 150° C.

Step 2-2: This step is a step of obtaining the compound (b-1) by nitrating the acetyl compound synthesized in the above Step 2-1. The nitration reaction can be performed under the same conditions as those generally used in nitration such as the conditions described in a document such as Jikken Kagaku Koza (Courses in Experimental Chemistry) 4th ed., vol. 20, edited by The Chemical Society of Japan, p. 394-404 (1992). Examples of the nitrating agent used in the reaction include concentrated nitric acid, concentrated nitric acid/acetic acid, concentrated nitric acid/concentrated sulfuric acid, potassium nitrate/concentrated sulfuric acid and fuming nitric acid/acetic anhydride. The reaction temperature is not particularly limited and is usually −20° C. to 70° C.

Step 2:

This step is a step of obtaining a compound (b-2) by deacetylation reaction of the compound (b-1). This reaction can be performed under the same conditions as those generally used in deprotection reaction of an acetyl group such as the conditions described in a document such as T. W. Green and P. G. M. Wuts, "Protective Groups in Organic Chemistry, Second Edition", John Wiley & Sons (1991), p. 351-352. The reaction can be performed in the presence of an acid such as hydrochloric acid, sulfuric acid or hydrobromic acid, for example. The reaction solvent is methanol, ethanol, toluene, propanol or the like. The reaction temperature is not particularly limited and is usually −20° C. to 150° C., and preferably room temperature to solvent reflux temperature.

Step 3:

This step is a step of obtaining a compound (b-3) by t-butoxycarbonylating the amino group of the compound (b-2).

The reaction can be performed under the same conditions as those generally used in t-butoxycarbonylation of an amino compound such as the conditions described in a document such as T. W. Green and P. G. M. Wuts, "Protective Groups in Organic Chemistry, Second Edition", John Wiley & Sons (1991), p. 327-330. The compound (b-3) can be obtained by reacting the compound (b-2) with di-tert-butyl dicarbonate using triethylamine as a base in a solvent such as tetrahydrofuran, for example.

Step 4:

This step is a method of obtaining a compound (b-4) by reducing the compound (b-3).

This reaction can be performed under the conditions generally used in reduction reaction of a nitro compound. Examples of the reaction include reduction by catalytic hydrogenation using a noble metal catalyst such as Raney nickel, palladium, ruthenium, rhodium or platinum; reduction by a metal such as iron; and reduction by sodium dithionite. In this case, reduction reaction with iron under neutral conditions using ammonium chloride is preferable, for example.

Step 5:

This step is a step of obtaining a compound (b-7) from the compound (b-4).

This reaction can be performed by a known method such as (1) a method of directly condensing the compound (b-4) with a compound (b-5) using a condensing agent (Method (1)), (2) a method of reacting a mixed acid anhydride of a compound (b-5) with the compound (b-4) (Method (2)), (3) a method of reacting an active ester of a compound (b-5) with the compound (b-4) (Method (3)) or (4) a method of reacting an acid chloride compound (b-6) with the compound (b-4) (Method (4)).

The compound (b-4) used in these reactions may be a free form or a salt.

Method (1):

The compound (b-7) can be obtained by directly condensing the compound (b-4) with the compound (b-5) using a condensing agent.

This reaction can be performed by a known method. Examples of the condensing agent include CDI (N,N'-carbonyldiimidazole), Bop (1H-1,2,3-benzotriazol-1-yloxy(tri(dimethylamino))phosphonium hexafluorophosphate), WSC (1-ethyl-3-(3-dimethylaminopropyl)carbodiimide hydrochloride), DCC (N,N-dicyclohexylcarbodiimide), diethylphosphoryl cyanide, PyBOP (benzotriazol-1-yloxytris(pyrrolidino)phosphonium hexafluorophosphate) and EDC.HCl (1-ethyl-3-(3-dimethylaminopropyl)carbodiimide hydrochloride).

The solvent in this reaction is not particularly limited insofar as it does not inhibit the reaction. Examples of the solvent include tetrahydrofuran, 1,4-dioxane, ethyl acetate, methyl acetate, dichloromethane, chloroform, N,N-dimethylformamide, toluene and xylene.

One equivalent to a large excess of the compound (b-5) is used with respect to the compound (b-4). One equivalent to a large excess of an organic base such as triethylamine may be added where necessary.

The reaction time is not particularly limited and is usually 0.5 to 48 hours, and preferably 0.5 to 24 hours. The reaction temperature varies according to the raw material used, the solvent and the like and is not particularly limited. Ice-cold temperature to solvent reflux temperature is preferable.

Method (2):

The compound (b-7) can be obtained by converting the compound (b-5) to a mixed acid anhydride and then reacting the mixed acid anhydride with the compound (b-4). The mixed acid anhydride can be synthesized by a known method. The synthesis is performed by reacting the compound (b-5) with a chloroformate such as ethyl chloroformate in the presence of a base such as triethylamine, for example. One to two equivalents of the chloroformate and the base are used with respect to the compound (b-5). The reaction temperature is −30° C. to room temperature, and preferably −20° C. to room temperature.

The step of condensing the mixed acid anhydride with the compound (b-4) is performed by reacting the mixed acid anhydride with the compound (b-4) in a solvent such as dichloromethane, tetrahydrofuran or N,N-dimethylformamide, for example. One equivalent to a large excess of the compound (b-4) is used with respect to the mixed acid anhydride.

The reaction time is not particularly limited and is usually 0.5 to 48 hours, and preferably 0.5 to 12 hours. The reaction temperature is −20° C. to 50° C., and preferably −20° C. to room temperature.

Method (3):

The compound (b-7) can be obtained by converting the compound (b-5) to an active ester and then reacting the active ester with the compound (b-4). The step of obtaining the active ester is performed by reacting the compound (b-5) with an active ester synthesis reagent in a solvent such as 1,4-dioxane, tetrahydrofuran or N,N-dimethylformamide in the presence of a condensing agent such as DCC, for example. Examples of the active ester synthesis reagent include N-hydroxysuccinimide. 1 to 1.5 equivalents of the active ester synthesis reagent and the condensing agent are used with respect to the compound (b-5). The reaction time is not particularly limited and is usually 0.5 to 48 hours, and preferably 0.5 to 24 hours.

The reaction temperature is −20° C. to 50° C., and preferably −20° C. to room temperature.

The step of condensing the active ester with the compound (b-4) is performed by reacting the active ester with the compound (b-4) in a solvent such as dichloromethane, tetrahydrofuran or N,N-dimethylformamide, for example. One equivalent to a large excess of the compound (b-4) is used with respect to the active ester. The reaction time is not particularly limited and is usually 0.5 to 48 hours, and preferably 0.5 to 24 hours. The reaction temperature is −20° C. to 50° C., and preferably −20° C. to room temperature.

Method (4):

The acylation reaction of obtaining the compound (b-7) from the compound (b-4) and the compound (b-6) can be performed under the same conditions as known conditions generally used.

Examples of the base used in the reaction include triethylamine, pyridine, potassium carbonate and diisopropylethylamine. The reaction temperature is not particularly limited and is usually −78° C. to solvent reflux temperature, and preferably −20° C. to room temperature. The solvent used in the reaction is not particularly limited insofar as it does not inhibit the reaction and allows the starting material to be dissolved therein to a certain extent. Preferable examples of the solvent include tetrahydrofuran, ether, toluene and dichloromethane.

Step 6:

This step is a step of obtaining the compound (I-a) by deprotection reaction of the t-butoxycarbonyl group of the compound (b-7).

The reaction can be performed under the same conditions as those generally used in deprotection reaction of a t-butoxycarbonyl group such as the conditions described in a document such as T. W. Green and P. G. M. Wuts, "Protective Groups in Organic Chemistry, Second Edition", John Wiley & Sons (1991), p. 327-330. The compound (I-a) can be obtained by reacting trifluoroacetic acid with the compound (b-7) in a solvent such as dichloromethane, for example.

The compound of the general formula (I) according to the present invention, wherein L is —C(=O)NR$^L$— (wherein R$^L$ is a C1-6 alkyl group which may have 1 to 3 substituents selected from Substituent Group α), can be obtained by further reacting the thus-obtained compound of the general formula (I) according to the present invention, wherein L is —C(=O)NH—, with a corresponding C1-6 alkyl halide by a common method.

When R$^3$ is a hydrogen atom in the general formula (I), the compound of the formula (I) according to the present invention, wherein R$^3$ is a C1-6 alkyl group which may have 1 to 3 substituents selected from Substituent Group α, a C1-6 alkylcarbonyl group which may have a substituent selected from Substituent Group α, a C6-10 arylcarbonyl group which may have 1 to 3 substituents selected from Substituent Group α, a C1-6 alkylsulfonyl group which may have 1 to 3 substituents selected from Substituent Group α, a C6-10 arylsulfonyl group which may have 1 to 3 substituents selected from Substituent Group α, a C3-10 carbocyclic group which may have 1 to 3 substituents selected from Substituent Group α or a 5- to 10-membered heterocyclic group which may have 1 to 3 substituents selected from Substituent Group α, can be obtained by further reacting the compound (I-a) obtained in General Preparation Method 2 with a corresponding halide compound such as a C1-6 alkyl halide, a C1-6 alkylcarbonyl halide, a C6-10 arylcarbonyl halide, a C1-6 alkylsulfonyl halide, a C6-10 arylsulfonyl halide, a C3-10 carbocyclic halide or a 5- to 10-membered heterocyclic halide.

3. General Preparation Method 3:

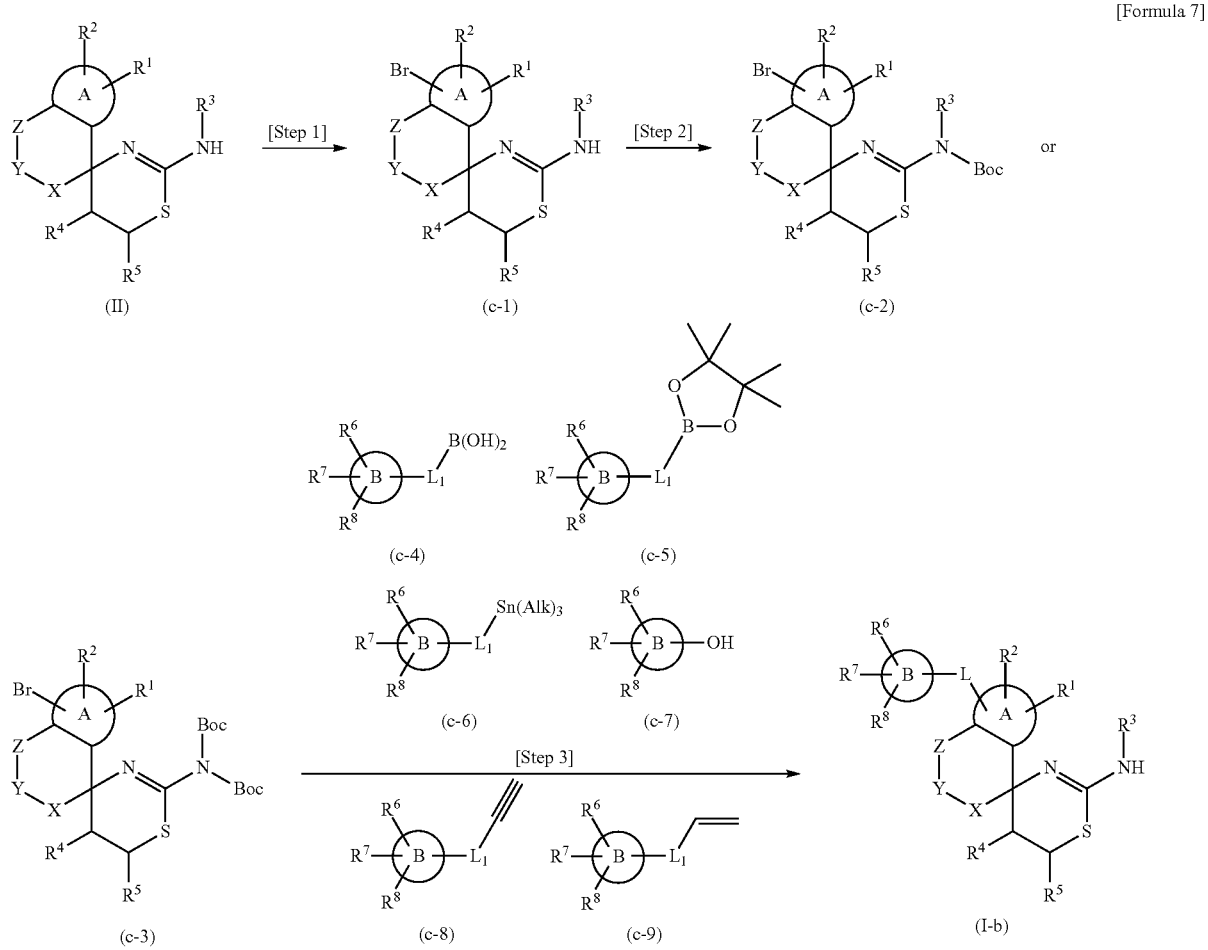

[Formula 7]

In the formula, $L_1$ represents a single bond or a C1-6 alkylene group in compounds (c-4), (c-5) and (c-6) and represents a single bond or a C1-4 alkylene group in compounds (c-8) and (c-9), L represents a single bond, an oxygen atom, a C1-6 alkylene group, a C2-6 alkenylene group or a C2-6 alkynylene group and Ring A, Ring B, $R^1$, $R^2$, $R^3$, $R^4$, $R^5$, $R^6$, $R^7$, $R^8$, X, Y and Z are as defined above.

General Preparation Method 3 is a method for preparing the compound (I-b) of the general formula (I), wherein L is a single bond, a double bond or a triple bond, from the compound (II) in three steps.

The compound (II) can be prepared from a commercially available product by the above General Preparation Method 1, and can also be prepared by a method described in Preparation Examples among Examples. The compounds (c-4), (c-5), (c-6), (c-7) and (c-8) each can be a commercially available product used as is, can also be prepared from a commercially available product by a known method, and can further be prepared by a method described in Preparation Examples among Examples.

Step 1:

This step is a step of obtaining a compound (c-1) by bromination reaction of the compound (II) in the system. This reaction can be performed by the same method as described in a document such as Holmberg, P.; Tedenborg, P.; Rosquvist, S.; Hohansson, A. M., Bioorg. Med. Chem. Lett.; 15 (3), 747-750 (2005), for example. Examples of the conditions used in the reaction include bromine/acetic acid, bromine/sodium carbonate/hexane and N-bromosuccinimide/methylene chloride. The reaction temperature is not particularly limited and is usually −20° C. to 50° C., and preferably −20° C. to room temperature.

Step 2:

This step is a step of obtaining a compound (c-2), or a compound (c-3) when $R^3$ is a hydrogen atom, by tert-butoxycarbonylating the compound (c-1). In this reaction, the compound (c-2) or (c-3) can be obtained by reacting the compound (c-1) with di-tert-butyl dicarbonate under the conditions generally used in t-butoxycarbonylation of an amide compound, for example, using 4-dimethylaminopyridine as a base in a solvent such as THF.

The solvent used in this reaction is not particularly limited insofar as it does not inhibit the reaction. Preferable examples of the solvent include organic solvents such as tetrahydrofuran, 1,4-dioxane, 1,2-dimethoxyethane, dichloromethane, DMF and acetonitrile, and mixed solvents thereof. Examples of the base used include triethylamine, 4-dimethylaminopyridine, DBU and mixtures thereof. A catalytic amount to an excess of, and more preferably 0.1 to 5 equivalents of the base is used with respect to the compound (c-1). Two equivalents to an excess of, and more preferably 2 to 10 equivalents of di-tert-butyl dicarbonate is used with respect to the compound (c-1). The reaction time is not particularly limited and is usually 5 minutes to 24 hours, and preferably 5 minutes to 12 hours. The reaction temperature is usually −20° C. to solvent reflux temperature, and more preferably 0° C. to solvent reflux temperature.

Step 3:

This step is a step of obtaining the compound (I-b) with the t-butoxycarbonyl group deprotected by coupling reaction of the compound (c-2) or (c-3) with a compound (c-4), (c-5), (c-6), (c-7), (c-8) or (c-9) using a transition metal. This reaction can be performed under the conditions usually used in coupling reaction using a transition metal (such as Suzuki-Miyaura reaction, Stille reaction, Sonogashira reaction, Heck reaction or a method described in Buckwald, S. L. et al., J Am Chem Soc (1999) 121 (18), 4369-4378).

The organometallic catalyst used in this reaction is not particularly limited. Preferable examples of the organometallic catalyst include metal catalysts such as tetrakis(triphenylphosphine)palladium (0), dichlorobis(triphenylphosphine)palladium (II), [1,1'-bis(diphenylphosphino)ferrocene]palladium (II) dichloride, bis(tert-butylphosphine) palladium (0), palladium (II) acetate and [1,3-bis(diphenylphosphino)propane]nickel (II), and mixtures of these metal catalysts. The amount of the organometallic catalyst used is about 0.001 to 0.5 equivalent with respect to the raw material. The amount of the compound (c-4), (c-5), (c-6), (c-7) (c-8) used is not particularly limited and is usually 1 to 6 equivalents with respect to the compound (c-2) or (c-3). The solvent used in this reaction is not particularly limited insofar as it does not inhibit the reaction. Preferable examples of the solvent include benzene, toluene, xylene, N,N-dimethylformamide, 1-methyl-2-pyrrolidone, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 48 hours, and preferably 0.5 to 24 hours.

A more preferable result such as an improved yield may be achieved by carrying out this reaction in the presence of a base or a salt. Such a base or salt is not particularly limited. Preferable examples of the base or salt include bases or salts such as sodium carbonate, potassium carbonate, barium hydroxide, cesium carbonate, potassium phosphate, potassium fluoride and solutions thereof, and triethylamine, N,N-diisopropylethylamine, lithium chloride and copper (I) iodide.

In Step 3, when $R^3$ is a hydrogen atom in the compound (c-1), the compound (I-b) can be synthesized by coupling reaction of the compound (c-1) with the compound (c-7) without protection of the amino group with a t-butoxycarbonyl group or the like.

When $R^3$ is a hydrogen atom in the general formula (I), the compound of the formula (I) according to the present invention, wherein $R^3$ is a C1-6 alkyl group which may have 1 to 3 substituents selected from Substituent Group α, a C1-6 alkylcarbonyl group which may have a substituent selected from Substituent Group α, a C6-10 arylcarbonyl group which may have 1 to 3 substituents selected from Substituent Group α, a C1-6 alkylsulfonyl group which may have 1 to 3 substituents selected from Substituent Group α, a C6-10 arylsulfonyl group which may have 1 to 3 substituents selected from Substituent Group α, a C3-10 carbocyclic group which may have 1 to 3 substituents selected from Substituent Group α or a 5- to 10-membered heterocyclic group which may have 1 to 3 substituents selected from Substituent Group α, can be obtained by further reacting the compound (I-b) obtained in General Preparation Method 3 with a corresponding halide compound such as a C1-6 alkyl halide, a C1-6 alkylcarbonyl halide, a C6-10 arylcarbonyl halide, a C1-6 alkylsulfonyl halide, a C6-10 arylsulfonyl halide, a C3-10 carbocyclic halide or a 5- to 10-membered heterocyclic halide.

The compound (I-b) obtained in General Preparation Method 3, wherein L is a C1-6 alkylene group, can be prepared by generating the compound (I-b), wherein L is a C2-6 alkenylene group or a C2-6 alkynylene group, by coupling reaction of the compound (c-2) or (c-3) with the compound (c-8) or (c-9) using a transition metal, and then subjecting the compound to reaction under the conditions usually used in reduction reaction, for example, using a catalyst such as palladium.

The compound of the formula (I) according to the present invention obtained in this manner can be converted to a pharmaceutically acceptable salt by a conventional method where necessary. The salt can be prepared by a method in which methods typically used in the field of organic synthetic chemistry and the like are appropriately combined. Specific examples of the method include neutralization titration of a free solution of the compound of the present invention with an acid solution. The compound of the formula (I) according to the present invention can be converted to a solvate by subjecting the compound to solvate forming reaction known per se where necessary.

The spiroaminodihydrothiazine derivative or pharmaceutically acceptable salt thereof according to the present invention has an extremely excellent Aβ production inhibitory effect or BACE1 inhibitory effect and is extremely useful as a prophylactic or therapeutic agent for a neurodegenerative disease caused by Aβ and typified by Alzheimer-type dementia.

The spiroaminodihydrothiazine derivative or pharmaceutically acceptable salt thereof according to the present invention can be formulated by a conventional method. Preferable examples of the dosage form include tablets, coated tablets such as film tablets and sugar-coated tablets, fine granules, granules, powders, capsules, syrups, troches, inhalants, suppositories, injections, ointments, eye drops, nasal drops, ear drops, cataplasms and lotions.

These solid preparations such as tablets, capsules, granules and powders can contain generally 0.01 to 100 wt %, and preferably 0.1 to 100 wt % of the spiroaminodihydrothiazine derivative or pharmaceutically acceptable salt thereof according to the present invention as an active ingredient.

The active ingredient is formulated by blending ingredients generally used as materials for a pharmaceutical preparation and adding an excipient, a disintegrant, a binder, a lubricant, a colorant and a corrective typically used, and adding a stabilizer, an emulsifier, an absorbefacient, a surfactant, a pH adjuster, a preservative and an antioxidant where necessary, for example, using a conventional method. Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrant used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those permitted to be added to pharmaceuticals. Examples of the corrective used include cocoa powder, menthol, empasm, mentha oil, borneol and cinnamon powder. Obviously, the ingredients are not limited to the above additive ingredients.

For example, an oral preparation is prepared by adding the spiroaminodihydrothiazine derivative or pharmaceutically acceptable salt thereof according to the present invention as an active ingredient, an excipient and, where necessary, a binder, a disintegrant, a lubricant, a colorant, a corrective and the like, and then forming the mixture into powder, fine granules, granules, tablets, coated tablets, capsules or the like by a conventional method. Obviously, tablets or granules may be appropriately coated, for example, sugar coated, where necessary.

For example, a syrup or an injection preparation is prepared by adding a pH adjuster, a solubilizer, an isotonizing agent and the like, and a solubilizing agent, a stabilizer and the like where necessary by a conventional method. The injection may be a previously prepared solution, or may be powder itself or powder containing a suitable additive, which is dissolved before use. The injection can contain usually 0.01 to 100 wt %, and preferably 0.1 to 100 wt % of the active ingredient. Further, a liquid preparation for oral administration such as a suspension or a syrup can contain usually 0.01 to 100 wt %, and preferably 0.1 to 100 wt % of the active ingredient.

For example, an external preparation can be prepared by any conventional method without specific limitations. As a base material, any of various materials usually used for a pharmaceutical, a quasi drug, a cosmetic or the like can be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like can be added where necessary. Further, ingredients such as an ingredient having a differentiation inducing effect, a blood flow enhancer, a bactericide, an antiphlogistic, a cell activator, vitamin, amino acid, a humectant and a keratolytic agent can be blended where necessary.

The dose of the spiroaminodihydrothiazine derivative or pharmaceutically acceptable salt thereof according to the present invention varies according to the degree of symptoms, age, sex, body weight, mode of administration, type of salt and specific type of disease, for example. Typically, the active ingredient is orally administered to an adult at about 30 μg to 10 g, preferably 100 μg to 5 g, and more preferably 100 μg to 1 g per day, or is administered to an adult by injection at about 30 μg to 1 g, preferably 100 μg to 500 mg, and more preferably 100 μg to 300 mg per day, in one or several doses, respectively.

The compound of the present invention can be converted to a chemical probe for capturing a target protein in a bioactive low-molecular compound. Specifically, the compound of the present invention can be converted to an affinity chromatography probe, a photoaffinity probe or the like by introducing a labeling group, a linker or the like into a moiety differing from a structural moiety essential for expression of activity of the compound by a technique described in J. Mass Spectrum. Soc. Jpn. Vol. 51, No. 5, 2003, p. 492-498 or WO 2007/139149, for example.

Examples of the labeling group, the linker or the like used for the chemical probe include groups shown in the following group consisting of (1) to (5):

(1) protein labeling groups such as photoaffinity labeling groups (such as a benzoyl group, a benzophenone group, an azido group, a carbonylazido group, a diaziridine group, an enone group, a diazo group and a nitro group) and chemical affinity groups (such as a ketone group substituted at the α-carbon atom with a halogen atom, a carbamoyl group, an ester group, an alkylthio group, Michael acceptors such as α,β-unsaturated ketones and esters, and an oxirane group), (2) cleavable linkers such as —S—S—, —O—Si—O—, monosaccharides (such as a glucose group and a galactose group) and disaccharides (such as lactose), and enzymatically cleavable oligopeptide linkers, (3) fishing tag groups such as biotin and 3-(4,4-difluoro-5,7-dimethyl-4H-3a,4a-diaza-4-bora-s-indacen-3-yl)propionyl, (4) detectable markers such as radioactive labeling groups such as $^{125}I$, $^{32}P$, $^{3}H$ and $^{14}C$; fluorescence labeling groups such as fluorescein, rhodamine, dansyl, umbelliferone, 7-nitrofurazanyl and 3-(4,4-difluoro-5,7-dimethyl-4H-3a,4a-diaza-4-bora-s-indacen-3-yl)propionyl; chemiluminescent groups such as luciferin and luminol; and heavy metal ions such as lanthanoid metal ions and radium ions, and (5) groups bound to solid-phase carriers such as glass beads, glass beds, microtiter plates, agarose beads, agarose beds, polystyrene beads, polystyrene beds, nylon beads and nylon beds.

When a probe is prepared by introducing a labeling group or the like selected from the group consisting of (1) to (5) above into the compound of the present invention in accordance with a method described in the above documents or the like, the probe can be used as a chemical probe for identification of labeled proteins useful for searching for novel drug targets, for example.

MODE FOR CARRYING OUT THE INVENTION

The present invention will be described more specifically below with reference to Preparation Examples, Examples and Test Example. However, the present invention is not limited thereto. The abbreviations used in Preparation Examples and Examples are conventional abbreviations known to a person skilled in the art. Some abbreviations are shown below.

THF: Tetrahydrofuran
DMF: N,N-Dimethylformamide
TFA: Trifluoroacetic acid
EDC.HCl: 1-Ethyl-3-(3-dimethylaminopropyl)carbodiimide hydrochloride
pTLC: Preparative thin-layer chromatography
LC-MS: Liquid chromatography-mass spectrometry
PyBOP: Benzotriazol-1-yloxytris(pyrrolidino)phosphonium hexafluorophosphate Chemical shifts in proton nuclear magnetic resonance spectra are recorded in δ units (ppm) relative to tetramethylsilane and coupling constants are recorded in Hertz (Hz). Patterns are designated as s: singlet, d: doublet, t: triplet, br: broad.

The "room temperature" in the following Examples and Preparation Examples typically refers to about 10° C. to about 35° C. "%" indicates wt % unless otherwise specified.

Preparation Example 1

Synthesis of 8-fluorochroman-4-one (Compound 1-3)

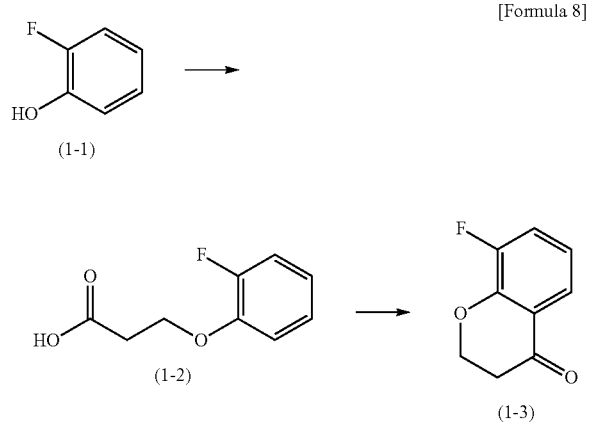

[Formula 8]

(1) Synthesis of 3-(2-fluorophenoxy)propionic acid (Compound 1-2)

(1-1) A solution of 2-fluorophenol (Compound 1-1, 3.0 g) in N,N-dimethylformamide (7.0 ml) was added to a solution of 50% sodium hydride (3.22 g) in N,N-dimethylformamide (100 ml) in a nitrogen atmosphere with cooling in an ice bath. After stirring at the same temperature for 30 minutes, a solution of 3-bromo-propionic acid (4.91 g) in N,N-dimethylformamide (8.0 ml) was added. The mixture was returned to room temperature and stirred at the same temperature for 24 hours. The pH was adjusted to 1 to 2 with 1 N hydrochloric acid (100 ml) to terminate the reaction. The aqueous layer was extracted with ethyl acetate, and the organic layer was washed with brine. The organic layer was dried over anhydrous magnesium sulfate, and the solvent was evaporated under reduced pressure. The residue was crystallized by adding a mixed solvent of 20% ethyl acetate-hexane to obtain the title compound (1.53 g).

(1-2) The title compound was synthesized by the following alternative method.

Potassium t-butoxide (2.42 g) was added to a solution of the compound 1-1 (2.20 g) in tetrahydrofuran (100 ml) at room temperature. After stirring for five minutes at the same temperature, beta-propiolactone (2.71 ml) was added. Because of heat generation, the mixture was moved to an ice bath and stirred at the same temperature for one hour. After further stirring at room temperature for four hours, the mixture was made acidic with 1 N hydrochloric acid to terminate the reaction. The aqueous layer was extracted with ethyl acetate, and the organic layer was washed with brine. The organic layer was dried over anhydrous magnesium sulfate, and the solvent was evaporated under reduced pressure. The residue was crystallized by adding a mixed solvent of 20% ethyl acetate-hexane to obtain the title compound (1.44 g).

1H NMR (400 MHz, DMSO-d6) (ppm): 2.73 (t, J=6.0 Hz, 2H), 4.24 (t, J=6.0 Hz, 2H), 6.90-7.00 (m, 1H), 7.09-7.24 (m, 3H), 12.41 (br. s., 1H).

(2) Synthesis of Compound 1-3

Polyphosphoric acid (7.0 g) was added to the compound 1-2 (450 mg), and the mixture was stirred at 100° C. for 3.5 hours. The heat source was turned off and the temperature was lowered to 75° C. At that time, crushed ice was gradually added to the reaction mixture with vigorous stirring. When the temperature was returned to room temperature, the reaction solution was added to ice water. The aqueous layer was extracted with diethyl ether, and the organic layer was sequentially washed with aqueous sodium bicarbonate and brine. The organic layer was dried over anhydrous magnesium sulfate, and the solvent was evaporated under reduced pressure. The residue was purified by silica gel column chromatography to obtain the title compound (273 mg).

1H NMR (400 MHz, CDCl$_3$) (ppm): 2.89 (t, J=6.4 Hz, 2H), 4.66 (t, J=6.4 Hz, 2H), 6.98 (td, J=4.4, 8.0 Hz, 1H), 7.29-7.34 (m, 1H), 7.71 (dt, J=1.5, 8.0 Hz, 1H).

The compounds described in Table 1 were similarly synthesized. The structural formulas and 1H-NMR data are shown in Table 1.

TABLE 1

| Structural formula | 1H-NMR (400MHz) • (ppm) |
| --- | --- |
| ![Br, F chroman-4-one] | 2.84-2.89 (m, 2H), 4.63-4.71 (m, 2H), 6.67 (dd, J = 8.8, 10.2 Hz, 1H), 7.68 (dd, J = 5.4, 8.8 Hz, 1H). |
| ![F chroman-4-one] | 2.81 (t, J = 6.6 Hz, 2H), 4.56 (t, J = 6.6 Hz, 2H), 6.67 (dd, J = 2.27, 9.85 Hz, 1 H), 6.75 (td, J = 2.27, 8.46 Hz, 1 H), 7.93 (dd, J = 6.8, 8.8 Hz, 1H). |
| ![F chroman-4-one] | 2.82 (t, J = 6.4 Hz, 2H), 4.54 (t, J = 6.4 Hz, 2H), 6.71 (ddd, J = 1.0, 8.3, 10.7, 1 H), 6.80 (dt, J = 1.0, 8.6 Hz, 1H), 7.41 (td, J = 6.1, 8.3 Hz, 1H). |

Preparation Example 2

Synthesis of 2,3,5',6'-tetrahydrospiro[chromene-4,4'-[1,3]thiazin]-2'-amine (Compound 1)

[Formula 9]

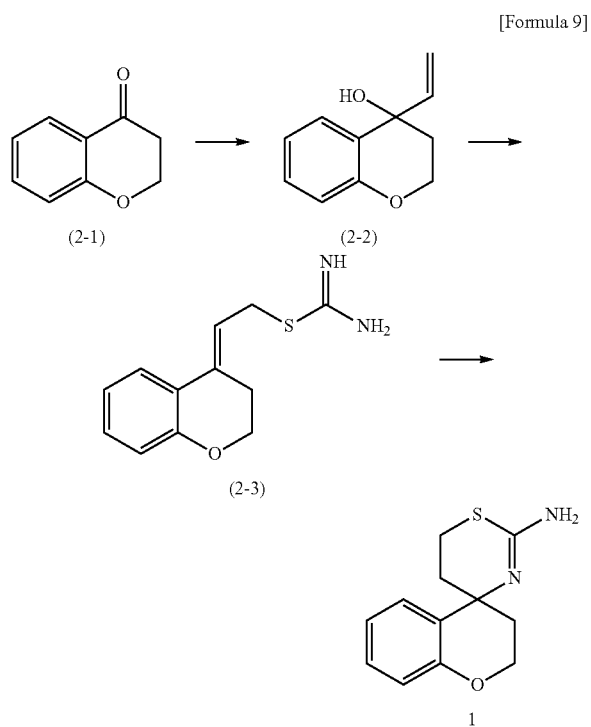

(1) Synthesis of 4-vinyl-chroman-4-ol (Compound 2-2)

Zinc chloride (461 mg) was added to vinylmagnesium chloride (1.48 M solution in tetrahydrofuran; 29.7 ml), and the mixture was stirred at room temperature for one hour. The reaction solution was cooled to 0° C., followed by dropwise addition of a solution of the compound 2-1 (5.00 g) in tetrahydrofuran (20.0 ml). The reaction solution was stirred at the same temperature for five hours. After confirming disappearance of the raw material, an ammonium chloride solution was added to the reaction mixture. The aqueous layer was extracted with ethyl acetate, and the organic layer was washed with brine. The organic layer was dried over anhydrous magnesium sulfate, and the solvent was evaporated under reduced pressure. The resulting crude product was purified by silica gel column chromatography to obtain the title compound (5.37 g).

$^1$H-NMR (400 MHz, CDCl$_3$) δ (ppm): 1.99 (ddd, J=2.4, 4.8, 13.6 Hz, 1H), 2.12 (m, 1H), 4.26 (ddd, J=4.0, 4.8, 8.8 Hz, 1H), 4.35 (dt, J=2.8, 10.8 Hz, 1H), 5.31 (dd, J=1.6, 10.6 Hz, 1H), 5.47 (dd, J=1.6, 16.8 Hz, 1H), 6.01 (dd, 10.6, 16.8 Hz, 1H), 6.85 (dd, J=1.2, 8.4 Hz, 1H), 6.90 (dt, J=1.2, 7.6 Hz, 1H), 7.20 (ddd, J=1.6, 7.6, 8.4 Hz, 1H), 7.28 (dd, J=1.6, 7.6 Hz, 1H).

(2) Synthesis of 2-[2-chroman-(4E)-ylideneethyl]-isothiourea (Compound 2-3)

Thiourea (2.75 g) was added to a solution of the compound 2-2 (5.30 g) in acetic acid (28.0 ml). After stirring at room temperature for four hours, the insoluble matter was removed by filtration through cotton plug and the filtrate was added dropwise to ether (200 ml). The mixture was cooled to 0° C. and stirred for four hours. The solid was allowed to stand overnight. The generated solid was removed by a glass filter, and the solvent in the filtrate was evaporated under reduced pressure. Ethyl acetate was added to the residual oil, followed by neutralization with aqueous sodium bicarbonate. Then, the generated white solid was collected by a glass filter and washed with water. The resulting solid was dried to obtain the title compound (3.10 g).

$^1$H-NMR (400 MHz, DMSO-d$_6$) δ (ppm): 2.74 (m, 2H), 3.74 (m, 2H), 4.17 (m, 2H), 6.18 (m, 1H), 6.83 (m, 1H), 6.90 (m, 1H), 7.16 (m, 1H), 7.59 (m, 1H).

(3) Synthesis of Compound 1

Trifluoromethanesulfonic acid (1.00 ml) was added dropwise to a solution of the compound 2-3 (1.00 g) in trifluoroacetic acid (5.00 ml) in an ice bath. The mixture was warmed to room temperature and stirred for two hours. The reaction mixture was added dropwise to aqueous sodium bicarbonate in an ice bath, to neutralize the reaction. The aqueous layer was extracted with ethyl acetate, and the organic layer was washed with aqueous sodium bicarbonate and brine. The organic layer was dried over anhydrous magnesium sulfate, and the solvent was evaporated under reduced pressure. The residue was purified by NH-silica gel column chromatography to obtain the title compound (300 mg).

$^1$H-NMR (400 MHz, CDCl$_3$) δ (ppm): 1.92 (ddd, J=3.0, 4.8, 14.0 Hz, 1H), 1.95 (ddd, J=4.0, 6.6, 14.0 Hz, 1H), 2.07 (ddd, J=4.2, 9.6, 14.0 Hz, 1H), 2.23 (ddd, J=4.2, 10.8, 14.0 Hz, 1H), 3.04 (ddd, J=4.2, 6.6, 12.8 Hz, 1H), 3.11 (ddd, J=4.0, 9.6, 12.8 Hz, 1H), 4.24 (ddd, J=3.0, 10.8, 11.6 Hz, 1H), 4.33 (ddd, J=4.2, 4.8, 11.6 Hz, 1H), 6.81 (dd, J=1.4, 8.1 Hz, 1H), 6.89 (dt, J=1.4, 7.2 Hz, 1H), 7.12 (ddd, J=1.6, 7.2, 8.1 Hz, 1H), 7.15 (dd, J=1.6, 7.6 Hz, 1H).

Preparation Example 3

Synthesis of N-(2'-amino(6-nitro-2,3,5',6'-tetrahydrospiro[chromene-4,4'-[1,3]thiazin]-6-yl)trifluoroacetamide (Compound 2)

[Formula 10]

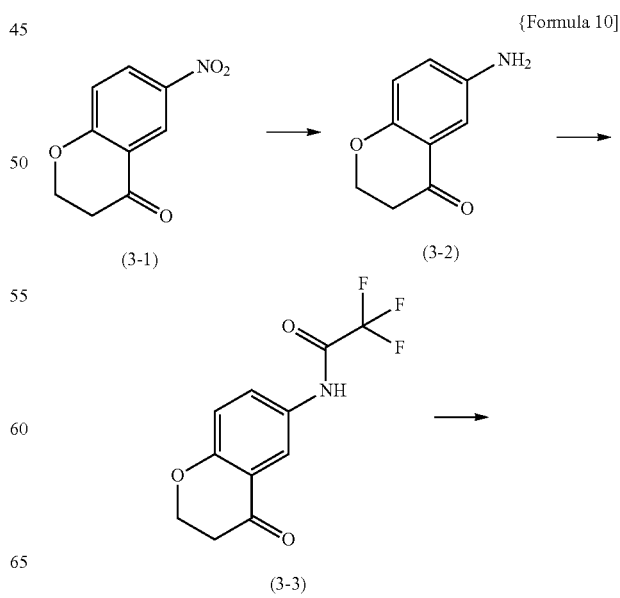

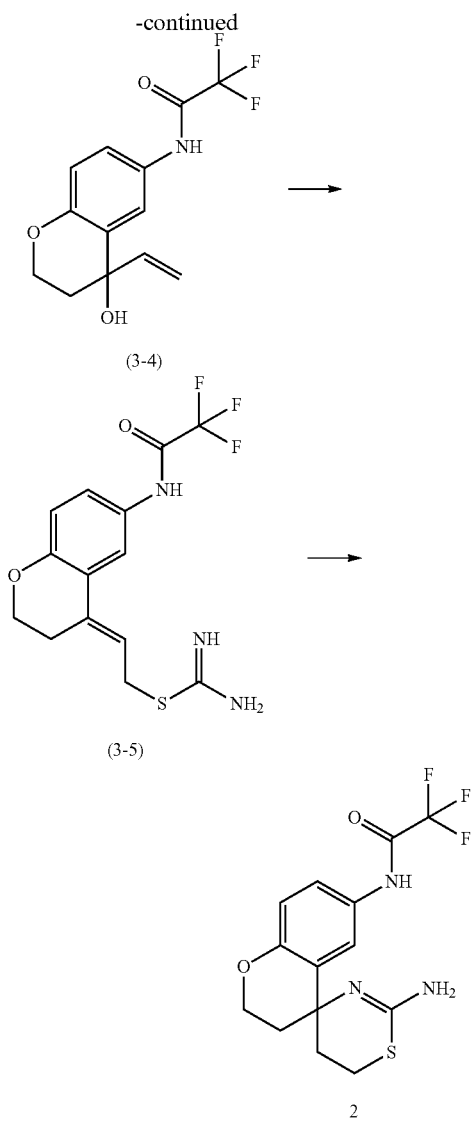

(3-4)

(3-5)

2

(1) Synthesis of 2,2,2-trifluoro-N-(4-oxochroman-6-yl)acetamide (Compound 3-3)

The compound 3-1 (1.0 g) was dissolved in acetone (50 ml). Tin dichloride dihydrate (3.66 g) was added and the mixture was heated under reflux overnight. After confirming completion of the reaction, the reaction mixture was cooled to room temperature. The solvent was evaporated under reduced pressure and aqueous sodium bicarbonate was added to the reaction mixture, followed by extraction with methylene chloride. The aqueous layer was reextracted with ethyl acetate. The organic layer was dried over anhydrous magnesium sulfate, and the solvent was evaporated under reduced pressure. The residue was purified by silica gel column chromatography. The resulting product (464 mg) was dissolved in methylene chloride (14 ml). Triethylamine (0.57 ml) and trifluoroacetic anhydride (0.57 ml) were added thereto in an ice bath, and the mixture was stirred at the same temperature for 20 minutes. Triethylamine (0.595 ml) was added and the mixture was further stirred in an ice bath for 40 minutes. After confirming disappearance of the raw material, an ammonium chloride solution was added to the reaction mixture to terminate the reaction. The aqueous layer was extracted with methylene chloride. The aqueous layer was further extracted with ethyl acetate, and the combined organic layers were dried over anhydrous magnesium sulfate. The pale yellow solid generated by evaporating the solvent under reduced pressure was collected by a Kiriyama funnel. The crude product was purified by silica gel column chromatography to obtain the title compound (644 mg).

1H NMR (400 MHz, DMSO-d6) (ppm): 2.82 (t, J=6.5 Hz, 2H), 4.55 (t, J=6.5 Hz, 2H), 7.11 (d, J=9.0 Hz, 1H), 7.79 (dd, J=9.0, 2.8 Hz, 1H), 8.10 (d, J=2.8 Hz, 1H), 11.30 (s, 1H)

(2) Synthesis of N-{4-[2-carbamimidoylsulfanyl-ethyl-(E)-idene]-chroman-6-yl}2,2,2-trifluoroacetamide (Compound 3-5)

A solution of the compound 3-3 (150 mg) in tetrahydrofuran (10.0 ml) was cooled to −78° C., and vinylmagnesium chloride (1.6 M solution in tetrahydrofuran; 1.09 ml) was added dropwise. The mixture was stirred at the same temperature for one hour and then stirred at room temperature for five hours. After confirming disappearance of the raw material, an ammonium chloride solution was added to the reaction mixture to terminate the reaction. The aqueous layer was extracted with ethyl acetate, and the organic layer was washed with brine. The organic layer was dried over anhydrous magnesium sulfate, and the solvent was evaporated under reduced pressure. The resulting crude product 3-4 (178 mg) was used for the next reaction without further purification.

Thiourea (66 mg) was added to a solution of the compound 3-4 (178 mg) in acetic acid (2.0 ml). The mixture was stirred at 50° C. for five hours and then stirred at room temperature overnight. The solvent was evaporated under reduced pressure, and then ethyl acetate was added to the residual oil, followed by neutralization with aqueous sodium bicarbonate. The aqueous layer was extracted with ethyl acetate, and the organic layer was washed with aqueous sodium bicarbonate and brine. The organic layer was dried over anhydrous magnesium sulfate, and the solvent was evaporated under reduced pressure. Ethyl acetate and diethyl ether were added to the residue. The generated pale yellow solid was collected by a Kiriyama funnel and washed with a mixed solvent of ethyl acetate and diethyl ether. The resulting solid was dried to obtain the title compound (26 mg).

$^1$H NMR (400 MHz, DMSO-$d_6$) (ppm): 2.74 (m, 2H), 4.11 (d, J=7.7 Hz, 2H), 4.18 (m, 2H), 6.07 (t, J=7.7 Hz, 1H), 6.89 (d, J=8.8 Hz, 1H), 7.45 (dd, J=2.4, 8.8 Hz, 1H), 7.92 (d, J=2.4 Hz, 1H)

(3) Synthesis of Compound 2

Trifluoromethanesulfonic acid (0.0459 ml) was added to a solution of the compound (3-5) (25.0 mg) in trifluoroacetic acid (0.459 ml) in an ice bath. The mixture was stirred at the same temperature for 1.5 hours and then stirred at room temperature for 1.5 hours. After confirming disappearance of the raw material, the reaction mixture was neutralized by adding it to aqueous sodium bicarbonate cooled in an ice bath. The aqueous layer was extracted with ethyl acetate, and the organic layer was washed with brine. The organic layer was dried over anhydrous sodium sulfate, and the solvent was evaporated under reduced pressure. The resulting crude product was crystallized from a methylene chloride solution to obtain the title compound (6.6 mg).

1H NMR (400 MHz, CDCl$_3$) (ppm): 2.07-2.14 (m, 1H), 2.26 (ddd, J=3.9, 7.9, 14.4 Hz, 1H), 2.42-2.53 (m, 2H), 3.14-

3.29 (m, 2H), 4.23-4.32 (m, 1H), 4.34-4.46 (m, 1H), 6.87 (d, J=8.9 Hz, 1H), 7.35 (d, J=2.6 Hz, 1H), 7.53 (dd, J=8.9, 2.6 Hz, 1H).

Preparation Example 4

Synthesis of 8-fluoro-2,3,5',6'-tetrahydrospiro [chromene-4,4'-[1,3]thiazin]-2'-amine (compound 3)

[Formula 11]

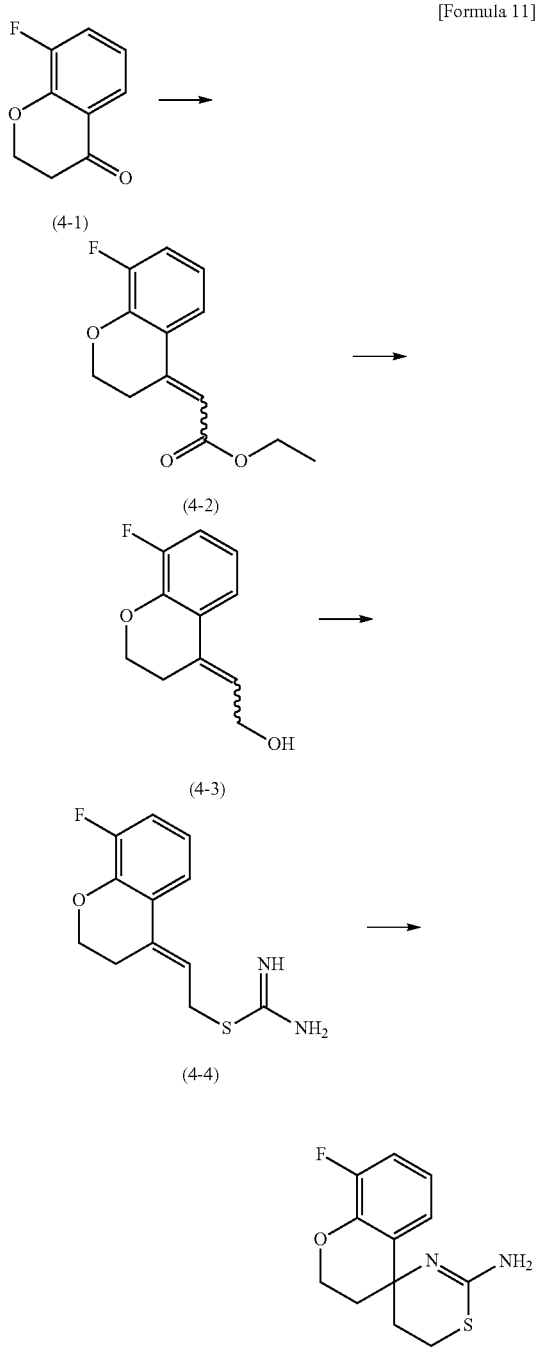

(1) Synthesis of ethyl (8-fluorochroman-4-ylidene)acetate (Compound 4-2)

A solution of N-butyllithium in hexane (1.6 N, 1.88 ml) was added to a solution of dicyclohexylamine (545.7 mg) in tetrahydrofuran (13.0 ml), cooled to −78° C. in a dry ice-acetone bath. After stirring at the same temperature for 10 minutes, a solution of ethyl(trimethylsilyl)acetate (482.3 mg) in tetrahydrofuran (2.5 ml) was added. After stirring at −78° C. for 10 minutes, a solution of the compound 4-1 (250.0 mg) in tetrahydrofuran (2.5 ml) was added. The mixture was stirred at −78° C. for one hour, and then returned to room temperature and further stirred for three hours. After confirming disappearance of the raw material, the reaction mixture was added to brine. The aqueous layer was extracted with ethyl acetate. The organic layer was dried over anhydrous sodium sulfate, and the solvent was evaporated under reduced pressure. The resulting crude product was purified by silica gel column chromatography to obtain the title compound (162 mg).

$^1$H NMR (400 MHz, CDCl$_3$) (ppm): 1.29 (t, J=7.1 Hz, 3H), 2.67 (td, J=1.3, 5.9 Hz, 2H), 4.22 (q, J=7.1 Hz, 2H), 4.44-4.49 (m, 2H), 5.76 (s, 1H), 6.78 (td, J=5.1, 8.1 Hz, 1H), 7.06 (ddd, J=1.5, 8.1, 10.9 Hz, 1H), 7.57 (dt, J=1.5, 8.1 Hz, 1H).

(2) Synthesis of (8-fluorochroman-4-ylidene)ethanol (Compound 4-3)

A solution of the compound 4-2 (162 mg) in diethyl ether (4.0 ml) was added dropwise over two minutes to a solution of lithium aluminium hydride (52.1 mg) in diethyl ether (8.0 ml), cooled in an ice bath in a nitrogen atmosphere. After stirring at the same temperature for two hours, ethyl acetate was slowly added to the reaction mixture. Then, water was added and the mixture was stirred for one hour. The aqueous layer was extracted with ethyl acetate, and the organic layer was sequentially washed with aqueous sodium bicarbonate and brine. The organic layer was dried over anhydrous magnesium sulfate, and the solvent was evaporated under reduced pressure. The resulting crude product was used for the next reaction without purification.

1H NMR (400 MHz, CDCl$_3$) (ppm): 2.61-2.65 (m, 2H), 4.43 (brt, J=5.2 Hz, 2H), 4.52 (d, J=6.4 Hz, 2H), 5.65 (t, J=6.4 Hz, 1H), 6.78-6.85 (m, 1H), 6.94 (brd, J=7.6 Hz, 1H), 7.02 (brt, J=9.5 Hz, 1H).

(3) Synthesis of Compound 3

Thiourea (7.7 mg) was added to a solution of the compound 4-3 (19.6 mg) in 48% hydrogen bromide (2.0 ml) at room temperature, and the mixture was stirred at 50° C. for two hours. After confirming disappearance of the raw material, the reaction mixture was neutralized by adding it to aqueous sodium bicarbonate cooled in an ice bath. The aqueous layer was extracted with ethyl acetate, and the organic layer was washed with brine. The organic layer was dried over anhydrous sodium sulfate, and the solvent was evaporated under reduced pressure. The resulting residue was dissolved in trifluoroacetic acid (0.49 ml), and then trifluoromethanesulfonic acid (0.1 ml) was added thereto in an ice bath. The mixture was stirred at the same temperature for 1.5 hours and then stirred at room temperature for 1.5 hours. After confirming disappearance of the raw material, the reaction mixture was neutralized by adding it to aqueous sodium bicarbonate cooled in an ice bath. The aqueous layer was extracted with ethyl acetate, and the organic layer was washed with brine. The organic layer was dried over anhydrous sodium sulfate, and the solvent was evaporated under reduced pressure. The residue was purified by NH-silica gel column chromatography to obtain the title compound (58.5 mg).

1H NMR (400 MHz, CDCl$_3$) (ppm): 1.93-2.01 (m, 2H), 2.05-2.14 (m, 1H), 2.28 (ddd, J=4.2, 10.5, 14.2 Hz, 1H), 3.02-3.09 (m, 1H), 3.09-3.17 (m, 1H), 4.32 (td, J=2.9, 11.0 Hz, 1H), 4.45 (td, J=4.5, 11.0 Hz, 1H), 6.79-6.86 (m, 1H), 6.92-6.99 (m, 2H).

Preparation Example 5

Synthesis of N-{4-[7-fluorochroman-(4E)-ylidene]ethyl}isothiourea (Compound 5-3)

(2) Synthesis of 2-{2-[7-fluorochroman-(4E)-ylidene]ethyl}-isothiourea (Compound 5-3)

(2-1) The compound 5-2 (214 mg) was dissolved in ethanol (6.0 ml). Thiourea (153 mg) was added and the mixture was heated under reflux for 10 hours. After confirming disappearance of the raw material, the solvent was evaporated under reduced pressure. The residue was purified by LCMS to obtain the title compound (33 mg).

$^1$H-NMR (400 MHz, CDCl$_3$) (ppm): 2.74 (m, 2H), 4.05 (d, J=7.9 Hz, 2H), 4.20 (t, J=5.8 Hz, 2H), 6.13 (t, J=7.9 Hz, 1H), 6.72 (dd, J=2.7, 10.3 Hz, 1H), 6.78 (ddd, J=2.7, 8.6, 9.0 Hz, 1H), 7.67 (dd, J=6.7, 8.9 Hz, 1H).

(2-2) The compound 5-3 can also be synthesized by the following alternative method.

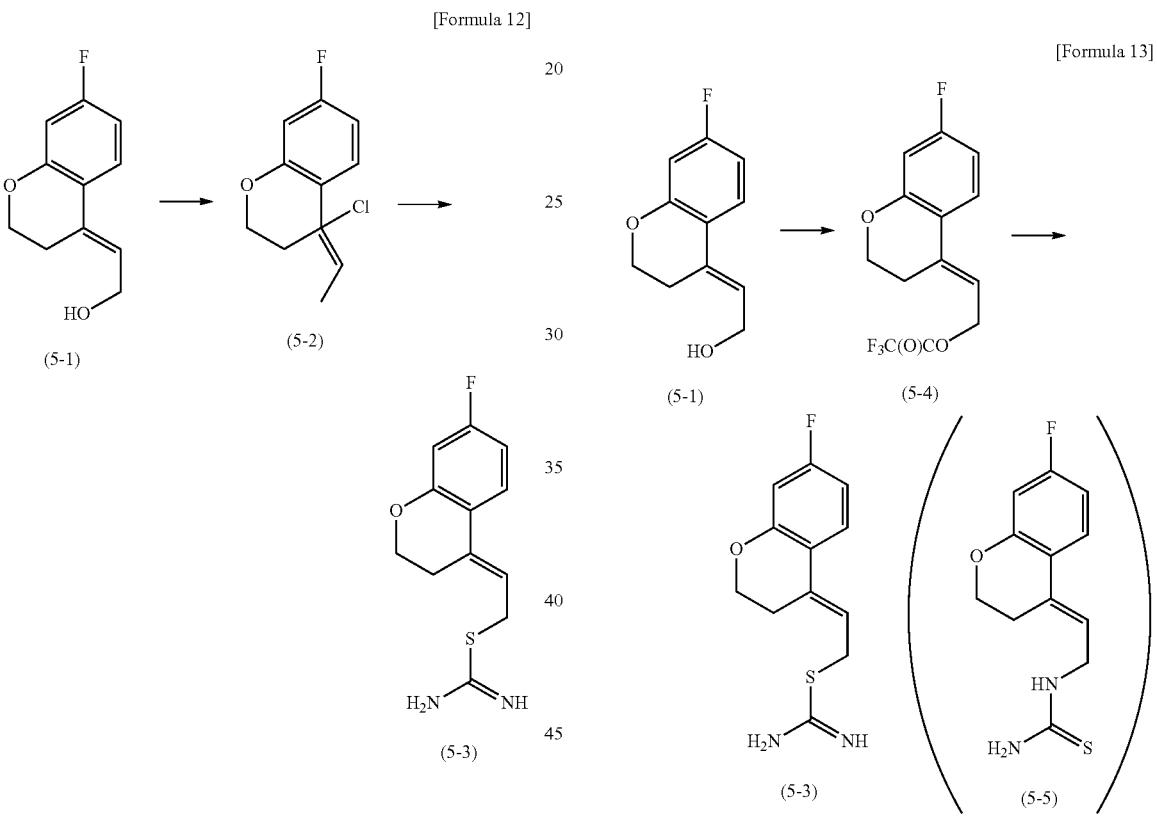

[Formula 12]

[Formula 13]

(1) Synthesis of 4-chloro-7-fluoro-4-vinylchroman (Compound 5-2)

Triethylamine (0.19 ml) was added to a solution of the compound 5-1 synthesized from 7-fluorochroman-4-one according to Example 4 (200 mg) in tetrahydrofuran (3.0 ml), cooled in an ice bath. A solution of methanesulfonyl chloride (177 mg) in tetrahydrofuran (2.0 ml) was added dropwise at the same temperature, followed by stirring for 1.5 hours. After confirming disappearance of the raw material, the reaction mixture was added to aqueous sodium bicarbonate to terminate the reaction. The aqueous layer was extracted with ethyl acetate. The aqueous layer was further extracted with ethyl acetate, and the combined organic layers were dried over anhydrous magnesium sulfate. The solvent was evaporated under reduced pressure to obtain the title compound (214 mg), which was used for the next reaction as a crude product.

(2) Synthesis of 2-(7-fluorochroman-4-ylidene)ethyl 2,2,2-trifluoroacetate (Compound 5-4)

Triethylamine (1.15 ml) was added to a solution of the compound 5-1 (1.0 g) in tetrahydrofuran (20 ml), cooled in an ice bath. A solution of trifluoroacetic anhydride (1.62 g) in tetrahydrofuran (2.5 ml) was added dropwise, and the mixture was stirred at the same temperature for one hour. After confirming disappearance of the raw material, the reaction mixture was added to aqueous sodium bicarbonate to terminate the reaction. The aqueous layer was extracted with ethyl acetate. The aqueous layer was further extracted with ethyl acetate, and the combined organic layers were dried over anhydrous magnesium sulfate. The solvent was evaporated under reduced pressure to obtain the title compound (1.42 g), which was used for the next reaction without purification.

¹H-NMR (400 MHz, CDCl₃) (ppm): 2.64 (m, 2H), 4.36 (m, 2H), 5.15 (d, J=7.1 Hz, 2H), 5.55 (t, J=7.1 Hz, 1H), 5.60 (dd, J=2, 7, 10.1 Hz, 1H), 6.66 (ddd, J=2.6, 8.3, 8.7 Hz, 1H), 7.08 (dd, J=6.4, 8.7 Hz, 1H).

(4) Synthesis of Compound 5-3

The compound 5-4 (1.41 g) was dissolved in ethanol (20 ml). Thiourea (0.92 g) was added and the mixture was heated under reflux for one hour. After confirming disappearance of the raw material, the solvent was evaporated under reduced pressure. The residue was purified by LCMS to obtain the compound 5-3 as a mixture with the compound 5-5 (9:1) (0.96 g).

¹H-NMR (400 MHz, CDCl₃) (ppm): 2.74 (m, 2H), 4.05 (d, J=7.9 Hz, 2H), 4.20 (t, J=5.8 Hz, 2H), 6.13 (t, J=7.9 Hz, 1H), 6.72 (dd, J=2.7, 10.3 Hz, 1H), 6.78 (ddd, J=2.7, 8.6, 9.0 Hz, 1H), 7.67 (dd, J=6.7, 8.9 Hz, 1H).

The compounds described in Table 2 were synthesized by the same method as described in Preparation Examples 2 to 4. The structural formulas and 1H-NMR data are shown in Table 2.

TABLE 2

| Compound No. | Structural formula | 1H-NMR (400MHz) • (ppm) |
|---|---|---|
| 4 | | 2.07-2.16 (m, 1 H), 2.17-2-25 (m, 1 H), 2.43-2.52 (m, 1 H), 2.64-2.74 (m, 1 H), 3.09-3.17 (m, 1 H), 3.26-3.36 (m, 1 H), 4.34 (ddd, J = 2.9, 8.3, 11.7 Hz, 1H), 4.47 (ddd, J = 3.3, 7.2, 11.7 Hz, 1H), 6.63 (dd, J = 8.8, 11.0 Hz, 1H) 7.47 (dd, J = 5.7, 8.8 Hz, 1H) |
| 5 | | 1.83-1.89 (m, 1 H), 1.91-2.02 (m, 2H), 2.16 (ddd, J = 14.1, 10.3, 4.2 Hz, 1 H), 2.95-3.02 (m, 1 H), 3.04-3.12 (m, 1 H), 4.11-4.18 (m, 1 H), 4.22-4.28 (m, 1 H), 6.67-6.71 (m, 1 H), 6.74-6.82 (m, 2 H). |
| 6 | | 2.21 (m, 2H), 2.63 (m, 2H), 3.20 (dt, J = 4.7, 13.4Hz, 1H), 3.33-3.44 (m, 1H), 4.20-4.36 (m, 2H), 6.76 (dd, J = 2.7, 10.6 Hz, 1H), 6.86 (ddd, J = 2.7, 8.6, 8.8 Hz, 1H), 7.41 (dd, J = 7.6, 8.8 Hz, 1H). |
| 7 | | 2.16 (m, 3H), 2.61 (tt, J = 3.3, 14.9 Hz, 1H), 3.20 (tt, J = 7.9, 13.4 Hz, 1H), 3.44 (t, J = 12.9 Hz, 1H), 4.24 (m, 2H), 6.79 (d, J = 8.4 Hz, 1H), 6.85 (ddd, J = 1.0, 8.3, 11.5 Hz, 1H), 7.33 (m, 1H). |

Example 1

Synthesis of (±)-N-[2'-amino-2,3,5',6'-tetrahydrospiro[chromene-4,4'-[1,3]thiazin]-6-yl]-5-chloropyridine-2-carboxamide (Compound 8)

[Formula 14]

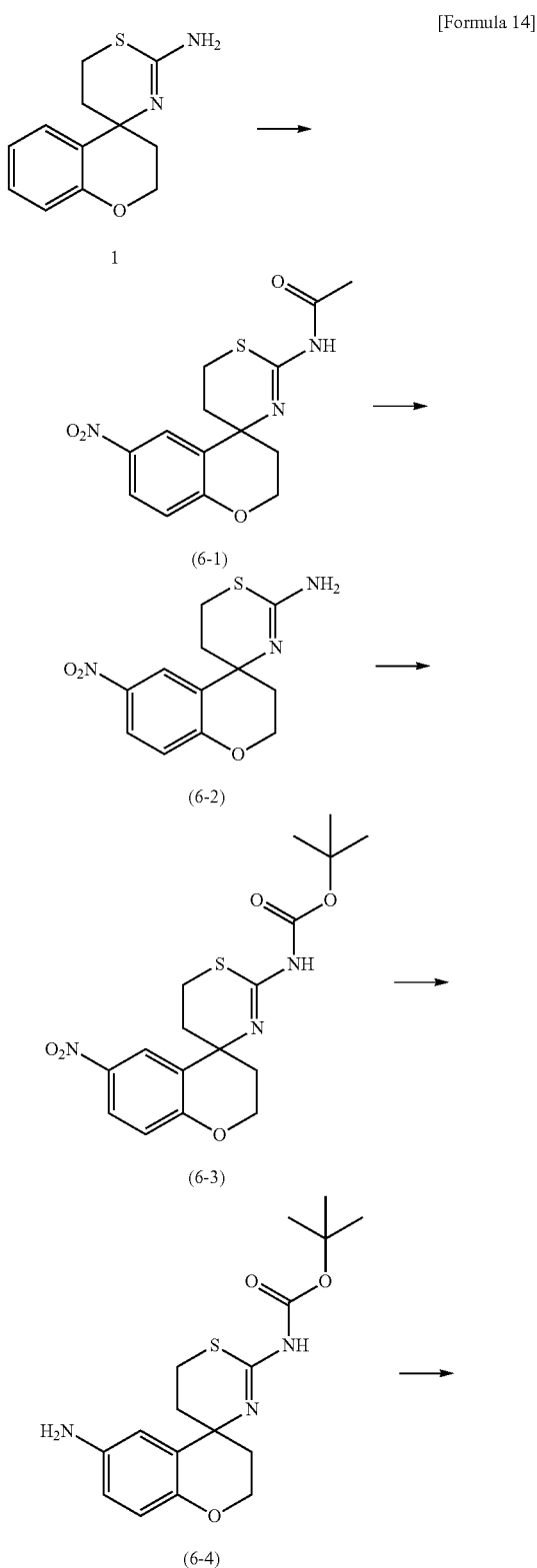

-continued

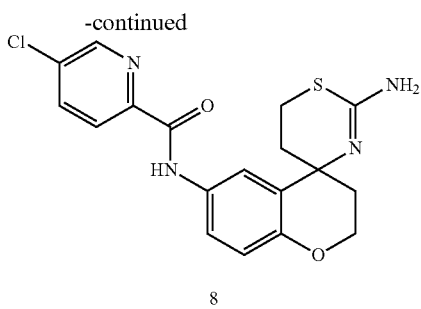

8

(1-1) 6-Nitro-2,3,5',6'-tetrahydrospiro[chromene-4, 4',-[1,3]thiazin]-2'-amine (Compound 6-2)

Fuming nitric acid (specific gravity: 1.53, 49.5 µl) was added dropwise to a solution of the compound 1 (280 mg) in acetic anhydride (10.0 ml) in an ice bath. The reaction solution was stirred at the same temperature for one hour, and then warmed to room temperature and stirred for three hours. Acetic anhydride (10.0 ml) was added to the reaction solution, followed by adding fuming nitric acid (specific gravity: 1.53, 400 µl). After confirming completion of the reaction, the reaction solution was diluted with ether and aqueous sodium bicarbonate was added, followed by stirring for one hour. The aqueous layer was extracted with ethyl acetate, and the organic layer was washed with aqueous sodium bicarbonate and brine. The organic layer was dried over anhydrous magnesium sulfate, and the solvent was evaporated under reduced pressure. The residue was purified by silica gel column chromatography to obtain the compound 6-1 as a mixture with a 8-nitro compound (360 mg).

Ethanol (10.0 ml) and concentrated sulfuric acid (330 µl) were added to the resulting nitro compound mixture (330 mg), and the mixture was heated under reflux for eight hours. After confirming completion of the reaction, the reaction mixture was cooled to room temperature. The reaction mixture was neutralized with aqueous sodium bicarbonate, followed by extraction with ethyl acetate. The organic layer was dried over anhydrous magnesium sulfate, and the solvent was evaporated under reduced pressure. The residue was purified by NH-silica gel column chromatography to obtain the title compound (82.0 mg).

$^1$H-NMR (400 MHz, CDCl$_3$) δ (ppm): 2.02 (m, 3H), 2.22 (m, 1H), 3.05 (m, 1H), 3.15 (m, 1H), 4.32 (m, 1H), 4.45 (m, 1H), 6.89 (d, J=9.0 Hz, 1H), 8.03 (d, J=9.0 Hz, 1H), 8.13 (s, 1H).

(1-2) The compound 6-1 can also be synthesized by the following alternative method.

Acetic anhydride (0.886 ml) was added to a solution of the compound 1 (1.1 g) in pyridine (6 ml) at room temperature, and the mixture was stirred at room temperature for 12 hours. The reaction solution was poured into ice-aqueous sodium bicarbonate, followed by extraction with ethyl acetate. The extract was dried over anhydrous magnesium sulfate. The drying agent was removed by filtration and the filtrate was concentrated under reduced pressure. The resulting crude product was purified by NH-silica gel column chromatography to obtain an N-acetyl compound of the compound 1 (N-(2,3,5',6'-tetrahydrospiro[chromene-4,4'-[1,3]thiazin]-2'-yl)acetamide) (1.1 g).

Nitric acid (specific gravity: 1.42, 1.0 ml) was added to a solution of the N-acetyl compound obtained as described above (1.3 g) in acetic acid (0.2 ml) at room temperature. The mixture was stirred at 50° C. for 30 minutes. Nitric acid (3.0 ml) was added to the solution at 50° C., and the mixture was stirred at 50° C. for 30 minutes. Nitric acid (2.0 ml) was further added at 50° C. and the mixture was stirred at 50° C. for 30 minutes. The reaction solution was slowly added to ice-aqueous sodium bicarbonate, followed by extraction with ethyl acetate. The extract was dried over anhydrous magnesium sulfate. The drying agent was removed by filtration and the filtrate was concentrated under reduced pressure. The crude product was purified by NH-silica gel column chromatography to obtain the compound 6-1 (0.93 g) as a mixture with a 8-nitro compound.

$^1$H-NMR (CDCl$_3$) δ: 2.00-2.40 (m, 4H), 2.03 (s, 3H, 8-isomer), 2.06 (s, 3H, 6-isomer), 2.95-3.10 (m, 2H), 4.13-4.60 (m, 2H), 6.90-6.95 (m, 1H, 6-isomer), 6.99 (t, J=8.0 Hz, 1H, 8-isomer), 7.36 (dd, J=1.6, 8.0 Hz, 1H, 8-isomer), 7.74 (dd, J=1.6, 8.0 Hz, 1H, 8-isomer), 8.03-8.10 (m, 2H, 6-isomer).

(2) t-Butyl (6-nitro-2,3,5',6'-tetrahydrospiro [chromene-4,4'-[1,3]thiazin]-2'-yl)carbamate (Compound 6-3)

The compound 6-2 (82.0 mg) was dissolved in tetrahydrofuran (5.00 ml), and triethylamine (631 µl) was added. Then, di-t-butyl dicarbonate (192 mg) was added to the reaction solution, and the mixture was stirred at room temperature for four days. After confirming completion of the reaction, the reaction solution was evaporated under reduced pressure. The residue was purified by NH-silica gel column chromatography to obtain the title compound (110 mg).

$^1$H-NMR (400 MHz, CDCl$_3$) δ (ppm): 1.48 (s, 9H), 2.00-2.30 (m, 4H), 3.02 (m, 1H), 3.14 (m, 1H), 4.39 (m, 2H), 6.93 (d, J=9.2 Hz, 1H), 8.08 (dd, J=2.8, 9.2 Hz, 1H), 8.14 (m, 1H).

(3-1) t-Butyl (±)-(6-amino-2,3,5',6'-tetrahydrospiro [chromene-4,4'-[1,3]thiazin]-2'-yl)carbamate (Compound 6-4)

The compound 6-3 (110 mg) was dissolved in ethanol (20.0 ml), and a solution of sodium dithionite (253 mg) in water was added dropwise at room temperature. A solution of sodium dithionite (253 mg) in water was further added to the reaction solution, and the mixture was stirred at room temperature. N,N-dimethylformamide (20.0 ml) was further added. After confirming completion of the reaction, the excess of ethanol was evaporated under reduced pressure. Water was added to the residue, and the aqueous layer was extracted with ethyl acetate. The organic layer was washed with water and brine and dried over anhydrous magnesium sulfate. The solvent was evaporated under reduced pressure and the residue was purified by NH-silica gel column chromatography to obtain the title compound (10.0 mg).

$^1$H-NMR (400 MHz, CDCl$_3$) δ (ppm): 1.46 (s, 9H), 2.05 (m, 1H), 2.15 (ddd, J=4.0, 6.4, 14.0 Hz, 1H), 2.26 (m, 1H), 2.38 (ddd, J=4.0, 10.0, 14.0 Hz, 1H), 3.10 (m, 2H), 4.20 (m, 2H), 6.59 (m, 2H), 6.68 (m, 1H).

(3-2) The compound 6-4 can also be synthesized by the following alternative method.

Iron (1.05 g) was added to a solution of the compound 6-3 (510 mg) in ethanol (18 ml)-aqueous ammonium chloride (1.8 ml), and the mixture was heated with stirring at 87° C. for 0.5 hour. The reaction solution was returned to room temperature and poured into ethyl acetate, and the insoluble matter was removed by filtration. The filtrate was concentrated under reduced pressure. Water was added to the residue, followed by extraction with ethyl acetate. The extract was washed with brine and dried over anhydrous magnesium sulfate. The drying agent was removed by filtration and the filtrate was concentrated under reduced pressure to obtain the title compound (0.40 g).

¹H-NMR (400 MHz, CDCl₃) δ (ppm): 1.46 (s, 9H), 2.05 (m, 1H), 2.15 (ddd, J=4.0, 6.4, 14.0 Hz, 1H), 2.26 (m, 1H), 2.38 (ddd, J=4.0, 10.0, 14.0 Hz, 1H), 3.10 (m, 2H), 4.20 (m, 2H), 6.59 (m, 2H), 6.68 (m, 1H).

(4) Synthesis of Compound 8

Toluene (3.00 ml) was added to 5-chloropyridine-2-carboxylic acid (5.86 mg) to form a suspension. After adding one drop of N,N-dimethylformamide, thionyl chloride (1.00 ml) was added. The reaction mixture was heated to 120° C. stirred at the same temperature for one hour. After cooling to room temperature, the solvent was evaporated under reduced pressure to obtain 5-chloropyridine-2-carboxylic acid chloride. The resulting acid chloride was suspended in tetrahydrofuran (1.00 ml), and the suspension was added dropwise to a solution of the compound 6-4 (10.0 mg) in tetrahydrofuran (2.00 ml) in an ice bath. After adding pyridine (11.3 µl) dropwise at the same temperature, the mixture was warmed to room temperature and stirred for 30 minutes. After confirming completion of the reaction, aqueous sodium bicarbonate was added to terminate the reaction. The aqueous layer was extracted with ethyl acetate, and the organic layer was washed with brine. The organic layer was dried over anhydrous magnesium sulfate, and the solvent was evaporated under reduced pressure. The resulting residue was dissolved in dichloromethane (2.00 ml). Trifluoroacetic acid (0.40 ml) was added and the mixture was stirred at room temperature for three hours. After confirming completion of the reaction, the reaction mixture was diluted with diethyl ether. Aqueous sodium bicarbonate was added to terminate the reaction. The aqueous layer was extracted with ethyl acetate, and the organic layer was dried over anhydrous magnesium sulfate. The solvent was evaporated under reduced pressure and the residue was purified by NH-silica gel column chromatography to obtain the title compound (7.8 mg).

¹H-NMR (400 MHz, CDCl₃) δ (ppm): 1.95 (ddd, J=2.8, 5.2, 14.0 Hz, 1H), 2.02 (ddd, J=4.4, 6.2, 14.0 Hz, 1H), 2.11 (ddd, J=4.4, 9.6, 14.0 Hz, 1H), 2.24 (ddd, J=4.0, 10.0, 14.0 Hz, 1H), 3.08-3.20 (m, 2H), 4.24 (dt, J=2.8, 11.2 Hz, 1H), 4.34 (dt, J=4.8, 10.8 Hz, 1H), 6.85 (d, J=8.8 Hz, 1H), 7.50 (d, J=2.4 Hz, 1H), 7.57 (dd, J=2.4, 8.8 Hz, 1H), 7.86 (dd, J=2.0, 8.4 Hz, 1H), 8.24 (dd, J=0.8, 8.4 Hz, 1H), 8.55 (dd, J=0.8, 2.0 Hz, 1H), 9.70 (s, 1H).

Example 2

Synthesis of (−)—N-[2'-amino-2,3,5',6'-tetrahydrospiro[chromene-4,4'-[1,3]thiazin]-6-yl]-5-chloropyridine-2-carboxamide (Compound 9)

[Formula 15]

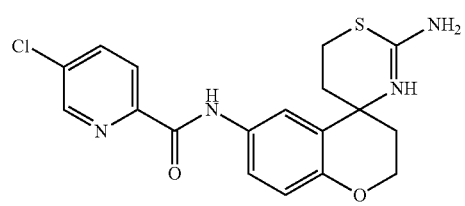

8

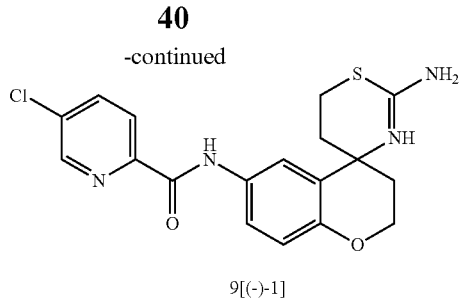

9[(−)-1]

The compound 8 (6 mg) was separated by CHIRALPAK™ OD-H manufactured by Daicel Chemical Industries, Ltd. (2 cm×25 cm, mobile phase: hexane:ethanol=8:2, flow rate: 20 ml/min). The component having a retention time of 22.5 to 25.0 minutes was collected and then purified by NH-silica gel column chromatography to obtain the title compound (2.0 mg; >99% ee).

ESI-MS; m/z 389 [M⁺+H].

¹H-NMR (400 MHz, CDCl₃) δ (ppm): 1.95 (ddd, J=2.8, 5.2, 14.0 Hz, 1H), 2.02 (ddd, J=4.4, 6.2, 14.0 Hz, 1H), 2.11 (ddd, J=4.4, 9.6, 14.0 Hz, 1H), 2.24 (ddd, J=4.0, 10.0, 14.0 Hz, 1H), 3.08-3.20 (m, 2H), 4.24 (dt, J=2.8, 11.2 Hz, 1H), 4.34 (dt, J=4.8, 10.8 Hz, 1H), 6.85 (d, J=8.8 Hz, 1H), 7.50 (d, J=2.4 Hz, 1H), 7.57 (dd, J=2.4, 8.8 Hz, 1H), 7.86 (dd, J=2.0, 8.4 Hz, 1H), 8.24 (dd, J=0.8, 8.4 Hz, 1H), 8.55 (dd, J=0.8, 2.0 Hz, 1H), 9.70 (s, 1H).

Example 3

Synthesis of t-Butyl (−)-(6-amino-2,3,5',6'-tetrahydrospiro[chromene-4,4'-[1,3]thiazin]-2'-yl)carbamate (Compound 10)

[Formula 16]

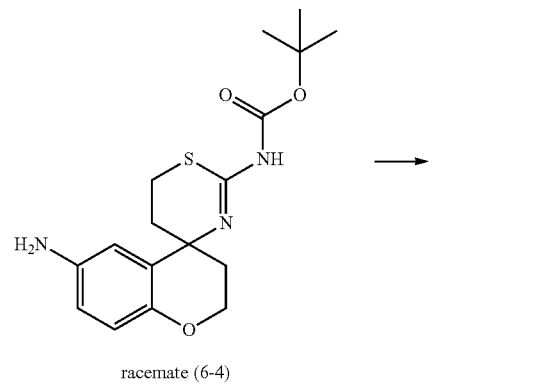

racemate (6-4)

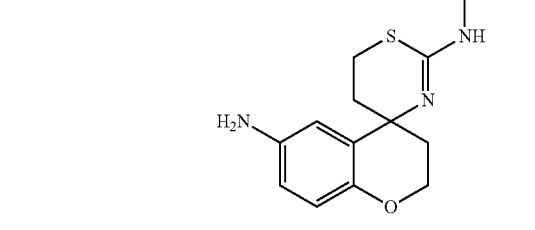

chiral 10[(−)-(6-4)]

The compound 6-4 obtained in Example 1-(3) (0.57 g) was separated by CHIRALPAK™ OJ-H manufactured by Daicel Chemical Industries, Ltd. (2 cm×25 cm, mobile phase: hexane:ethanol=6:4, flow rate: 10 ml/min). The component having a retention time of 28 to 34 minutes was collected to obtain the title compound (0.22 g, 97% ee).

Example 4

Synthesis of (−)—N-(2'-amino-2,3,5',6'-tetrahydrospiro[chromene-4,4'-[1,3]thiazin]-6-yl)-5-cyanopyridine-2-carboxamide (Compound 11)

[Formula 17]

(1) Synthesis of methyl 5-cyanopyridine-2-carboxylate (Compound 9-2)

A mixture of the compound 9-1 (2.8 g) and copper cyanide (3.6 g) in NMP (30 ml) was heated with stirring at 170° C. for 1.5 hours. Water was added to the reaction solution at room temperature, and the insoluble matter was removed by filtration. The filtrate was extracted with ethyl acetate. The extract was washed with brine and then dried over anhydrous magnesium sulfate. The drying agent was removed by filtration and the filtrate was concentrated under reduced pressure. The resulting crude product was purified by silica gel column chromatography to obtain the title compound (920 mg).

$^1$H-NMR (400 MHz, CDCl$_3$) δ (ppm): 4.06 (s, 3H), 8.16 (dd, J=2.0, 8.0 Hz, 1H), 8.27 (d, J=8.0 Hz, 1H), 9.01 (d, J=2.0 Hz, 1H).

(2) Synthesis of 5-cyanopyridine-2-carboxylic acid (Compound 9-3)

A solution of the compound 9-2 (920 mg) and a 5 N sodium hydroxide solution (2.26 ml) in ethanol (30 ml) was stirred at room temperature for 10 minutes. 5 N hydrochloric acid (5.2 ml) was added to the reaction solution at room temperature, followed by extraction with ethyl acetate. The extract was dried over anhydrous magnesium sulfate. The drying agent was removed by filtration and the filtrate was concentrated under reduced pressure to obtain the title compound (800 mg).

$^1$H-NMR (400 MHz, DMSOd$_6$) δ (ppm): 8.18 (d, J=8.0 Hz, 1H), 8.51 (dd, J=2.0, 8.0 Hz, 1H), 9.12-9.18 (m, 1H).

(3) Synthesis of tert-butyl {6-[(5-cyanopyridine-2-carbonyl)amino]-2,3,5',6'-tetrahydrospiro[chromene-4,4'-[1,3]thiazin]-2'-yl}carbamate (Compound 9-4)

PyBOP (74.5 mg) was added to a solution of the compound 10 obtained in Example 3 (25.0 mg), N,N-diisopropylethylamine (0.0624 ml) and 5-cyanopyridine-2-carboxylic acid (Compound 9-3) (16.9 mg) in dichloromethane (5.0 ml) at room temperature. The mixture was stirred at room temperature for one hour. The reaction solution was poured into aqueous sodium bicarbonate, followed by extraction with ethyl acetate. The extract was washed with brine and dried over anhydrous magnesium sulfate. The drying agent was removed by filtration and the filtrate was concentrated under reduced pressure. The crude product was purified by silica gel column chromatography to obtain the title compound (35 mg).

ESI-MS; m/z 480 [M$^+$+H].

(4) Synthesis of Compound 11

Trifluoroacetic acid (1.0 ml) was added to a solution of the compound 9-4 (35 mg) in dichloromethane (3.0 ml), and the reaction solution was stirred at room temperature for 1.5 hours. The reaction solution was poured into aqueous sodium bicarbonate, followed by extraction with ethyl acetate. The extract was washed with brine and dried over anhydrous magnesium sulfate. The drying agent was removed by filtration and the filtrate was concentrated under reduced pressure. The crude product was purified by NH-silica gel column chromatography to obtain the title compound (26.1 mg). ESI-MS; m/z 380 [M$^+$+H].

$^1$H-NMR (400 MHz, CDCl$_3$) δ (ppm): 1.90-2.15 (m, 3H), 2.24 (ddd, J=4.0, 10.4, 14.0 Hz, 1H), 3.05-3.2 (m, 2H), 4.25 (dt, J=3.2, 10.8 Hz, 1H), 4.35 (dt, J=4.8, 10.8 Hz, 1H), 6.86 (d, J=8.8 Hz, 1H), 7.50 (d, J=2.8 Hz, 1H), 7.58 (dd, J=2.8, 8.8 Hz, 1H), 8.19 (dd, J=2.0, 8.0 Hz, 1H), 8.42 (d, J=8.0 Hz, 1H), 8.88 (d, J=2.0 Hz, 1H), 9.74 (s, 1H).

Example 5

Synthesis of N-(2'-amino-2,3,5',6'-tetrahydrospiro[chromene-4,4'-[1,3]thiazin]-6-yl)-5-trifluoromethylpyridine-2-carboxamide (Compound 12)

[Formula 18]

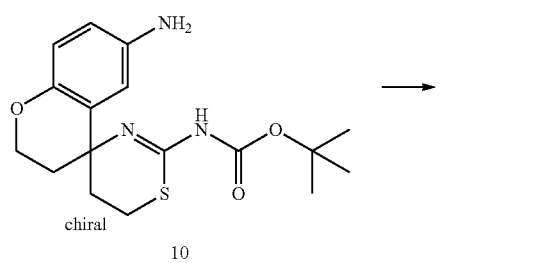

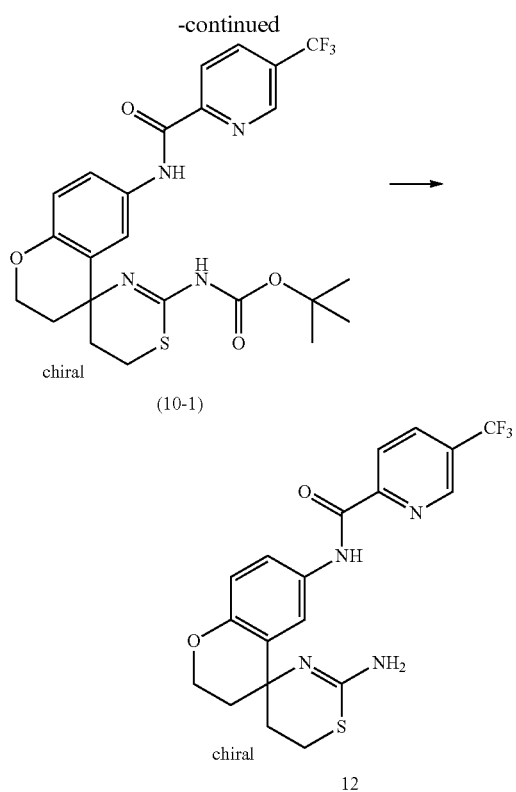

(1) Synthesis of tert-butyl {6-[(5-trifluoromethylpyridine-2-carbonyl)amino]-2,3,5',6'-tetrahydrospiro[chromene-4,4'-[1,3]thiazin]-2'-yl}carbamate (Compound 10-1)

PyBOP (59.6 mg) was added to a solution of the compound 10 (20.0 mg), N,N-diisopropylethylamine (0.0499 ml) and 5-trifluoromethylpyridine-2-carboxylic acid (13.5 mg) in dichloromethane (3.0 ml) at room temperature. The mixture was stirred at room temperature for one hour. The reaction solution was poured into aqueous sodium bicarbonate, followed by extraction with ethyl acetate. The extract was washed with brine and dried over anhydrous magnesium sulfate. The drying agent was removed by filtration and the filtrate was concentrated under reduced pressure. The crude product was purified by silica gel column chromatography to obtain the title compound (30 mg).

ESI-MS; m/z 523 [M$^+$+H].

(2) Synthesis of Compound 12

Trifluoroacetic acid (0.857 ml) was added to a solution of the compound 10-1 (30 mg) in dichloromethane (3.0 ml), and the reaction solution was stirred at room temperature for 1.5 hours. The reaction solution was poured into aqueous sodium bicarbonate, followed by extraction with ethyl acetate. The extract was washed with brine and dried over anhydrous magnesium sulfate. The drying agent was removed by filtration and the filtrate was concentrated under reduced pressure. The crude product was purified by NH-silica gel column chromatography to obtain the title compound (13.0 mg).

ESI-MS; m/z 423 [M$^+$+H].

$^1$H-NMR (400 MHz, CDCl$_3$) δ (ppm): 1.90-2.16 (m, 3H), 2.24 (ddd, J=4.4, 10.4, 14.0 Hz, 1H), 3.06-3.22 (m, 2H), 4.25 (dt, J=2.8, 11.2 Hz, 1H), 4.35 (dt, J=4.8, 11.2 Hz, 1H), 6.86 (d, J=8.8 Hz, 1H), 7.53 (d, J=2.4 Hz, 1H), 7.58 (dd, J=2.4, 8.8 Hz, 1H), 8.15 (dd, J=1.6, 8.0 Hz, 1H), 8.42 (d, J=8.0 Hz, 1H), 8.87 (s, 1H), 9.80 (s, 1H).

The compounds described in Table 3 were synthesized in the same manner as in Example 5. The structural formulas and $^1$H-NMR data are shown in Table 3.

TABLE 3

| Compound No. | Structural formula | 1H-NMR (400MHz) • (ppm) |
|---|---|---|
| 13 | chiral | 1.86-2.16 (m, 3H), 2.16-2.28 (m, 1H), 3.02-3.22 (m, 2H), 4.16-4.40 (m, 2H), 6.80-6.88 (m, 1H), 7.37 (ddd, J = 2.4, 8.0, 11.4 Hz, 1H), 7.46-7.56 (m, 2H), 8.34 (d, J = 1.6 Hz, 1H), 9.47 (s, 1H). |
| 14 | chiral | 1.88-2.16 (m, 3H), 2.24 (ddd, J = 4.0, 10.4, 14.0 Hz, 1H), 3.04-3.22 (m, 2H), 4.24 (dt, J = 2.8, 11.2 Hz, 1H), 4.34 (dt, J = 4.4, 11.2 Hz, 1H), 6.85 (d, J = 8.8 Hz, 1H), 7.44-7.64 (m, 3H), 8.32 (dd, J = 4.8, 8.8 Hz, 1H), 8.44 (d, J = 2.8 Hz, 1H), 9.67 (s, 1H). |
| 15 | chiral | 1.94-2.22 (m, 4H), 3.04-3.28 (m, 2H), 4.22-4.32 (m, 2H), 6.81 (d, J = 8.8 Hz, 1H), 7.55 (d, J = 2.4, 8.8 Hz, 1H), 7.65 (d, J = 2.4 Hz, 1H), 9.10 (s, 2H). |
| 16 | chiral | 1.86-2.16 (m, 3H), 2.24 (ddd, J = 4.0, 10.4, 14.0 Hz, 1H), 3.06-3.22 (m, 2H), 4.24 (dt, J = 2.8, 11.2 Hz, 1H), 4.34 (dt, J = 4.4, 11.2 Hz, 1H), 6.85 (d, J = 8.8 Hz, 1H), 7.50 (d, J = 2.8 Hz, 1H), 7.56 (dd, J = 2.8, 8.8 Hz, 1H), 8.02 (dd, J = 2.0, 8.4 Hz, 1H), 8.17 (d, J = 8.4 Hz, 1H), 8.65 (d, J = 2.0 Hz, 1H), 9.70 (s, 1H). |

TABLE 3-continued

| Compound No. | Structural formula | 1H-NMR (400MHz) • (ppm) |
|---|---|---|
| 17 | 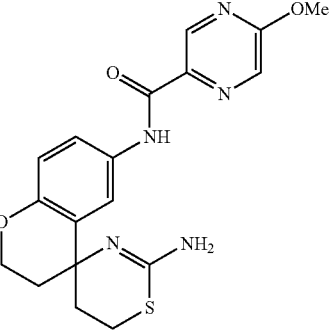 chiral | 1.88-2.16 (m, 3H), 2.18-2.30 (m, 1H), 3.04-3.22 (m, 2H), 4.06 (s, 3H), 4.18-4.38 (m, 2H), 6.84 (d, J = 8.8 Hz, 1H), 7.49 (d, J = 2.8 Hz, 1H), 7.53 (dd, J = 2.8, 8.8 Hz, 1H), 8.14 (s, 1H), 9.01 (s, 1H), 9.37 (s, 1H). |

Example 6

Synthesis of 6-(5-methoxypyridin-3-yl)-2,3,5',6'-tetrahydrospiro[chromene-4,4'-[1,3]thiazin]-2'-amine (Compound 21)

[Formula 19]

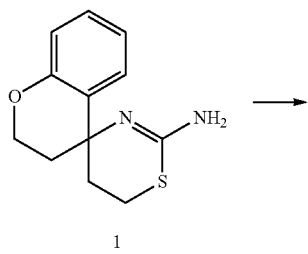

1

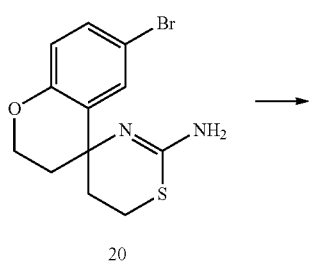

20

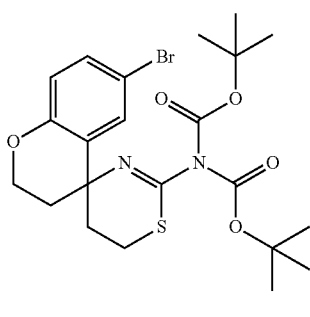

(11-1)

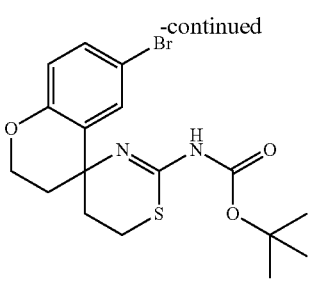

(11-2)

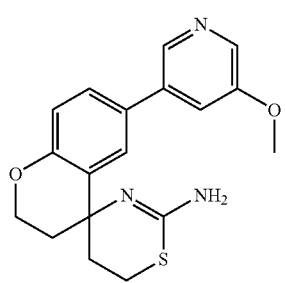

21

(1) Synthesis of 6-bromo-2,3,5',6'-tetrahydrospiro[chromene-4,4'-[1,3]thiazin]-2'-amine (Compound 20)

Bromine (382 mg) was added to a solution of the compound 1 (560 mg) in acetic acid (12.0 ml) at room temperature, followed by stirring for 30 minutes. After confirming disappearance of the raw material, the reaction mixture was neutralized by adding it to a 10% sodium hydroxide solution cooled in an ice bath. The aqueous layer was extracted with ethyl acetate, and the organic layer was washed with brine. The organic layer was dried over anhydrous magnesium sulfate, and the solvent was evaporated under reduced pressure. The resulting crude product was purified by silica gel column chromatography to obtain the title compound (580 mg).

1H NMR (400 MHz, CDCl$_3$) (ppm): 1.93 (ddd, J=3.0, 5.0, 14.1 Hz, 1H), 2.00-2.05 (m, 2H), 2.22 (ddd, J=4.1, 10.3, 14.1 Hz, 1H), 3.02-3.09 (m, 1H), 3.10-3.18 (m, 1H), 4.18-4.25 (m, 1H), 4.33 (ddd, J=4.4, 4.7, 11.3 Hz, 1H), 6.70 (d, J=8.6 Hz, 1H), 7.20-7.24 (m, 1H), 7.25 (d, J=2.4 Hz, 1H).

(2) Synthesis of di-tert-butyl (6-bromo-2,3,5',6'-tetrahydrospiro[chromene-4,4'-[1,3]thiazin]-2'-yl)imidazodicarbonate (Compound 11-1) and tert-butyl (6-bromo-2,3,5',6'-tetrahydrospiro[chromene-4,4'-[1,3]thiazin]-2'-yl)carbonate (Compound 11-2)

The compound 20 (139 mg) was dissolved in methylene chloride (15 ml), and di-t-butyl dicarbonate (387 mg) was added. Then, N,N-dimethylaminopyridine (217 mg) was added and the mixture was stirred at room temperature for 3.5 hours. After confirming disappearance of the raw material, the reaction mixture was added to a saturated ammonium chloride solution. The aqueous layer was extracted with methylene chloride, and the organic layer was dried over anhydrous magnesium sulfate. The solvent was evaporated under reduced pressure and the residue was purified by silica gel column chromatography to obtain the compounds 11-1 and 11-2 [(11-1) 144 mg, (11-2) 52.3 mg].

1H NMR (400 MHz, METHANOL-d4) (ppm): 1.59 (s, 18H), 1.87-1.98 (m, 2H), 2.06-2.17 (m, 2H), 2.37 (td, J=4.0, 14.6 Hz, 1H), 3.21 (td, J=4.2, 12.9 Hz, 1H), 3.45 (dt, J=3.6, 12.9 Hz, 1H), 4.28-4.37 (m, 1H), 6.80 (d, J=8.7 Hz, 1H), 7.28 (d, J=2.4 Hz, 1H), 7.26 (dd, J=2.4, 8.7 Hz, 1H) of compound 11-1.

1H NMR (400 MHz, METHANOL-d4) (ppm): 1.60 (s, 9H), 2.03-2.12 (m, 1H), 2.18-2.29 (m, 1H), 3.16-3.23 (m, 1H), 3.36-3.43 (m, 1H), 4.31-4.37 (m, 2H), 6.80 (d, J=8.7 Hz, 1H), 7.26 (d, J=2.4 Hz, 1H), 7.32 (dd, J=2.4, 8.7 Hz, 1H) of compound 11-2.

(3) Synthesis of Compound 21

3-Methoxy-5-(4,4,5,5-tetramethyl-1,3,2-dioxaborolan-2-yl)pyridine (14.9 mg) was added to a solution of the compound 11-1 (25 mg) in N,N-dimethylformaldehyde (2 ml). Subsequently, a 1 M sodium bicarbonate solution (0.12 ml) and palladium-triphenyl phosphine (2.8 mg) were added and the mixture was stirred in a nitrogen atmosphere at 100° C. for 12 hours. After confirming disappearance of the raw material, water was added to the reaction mixture. The aqueous layer was extracted with ethyl acetate, and the organic layer was washed with brine. The organic layer was dried over anhydrous magnesium sulfate, and the solvent was evaporated under reduced pressure. The resulting crude product was purified by silica gel column chromatography to obtain the title compound (8.6 mg).

1H NMR (400 MHz, CDCl₃) (ppm): 2.11-2.26 (m, 2H), 2.37-2.53 (m, 2H), 3.13-3.29 (m, 2H), 3.92 (s, 3H), 4.27-4.36 (m, 1H), 4.40-4.47 (m, 1H), 6.93-6.98 (m, 1H), 7.36-7.44 (m, 3H), 8.23 (br. s., 1H), 8.37 (br. s., 1H).

The compounds described in Table 4 were synthesized in the same manner as in Example 6-(3). The structural formulas and ¹H-NMR data are shown in Table 4.

TABLE 4

| Compound No. | Structural formula | 1H-NMR (400MHz) • (ppm) |
|---|---|---|
| 22 | (structure with two Cl substituents on phenyl) | 2.04 (ddd, J = 3.0, 5.3, 13.9 Hz, 1 H), 2.09-2.17 (m, 1 H), 2.19-2.27 (m, 1 H), 2.33 (ddd, J = 3.6, 9.9, 13.9 Hz, 1 H), 3.07-3.15 (m, 1H), 3.18-3.26 (m, 1 H), 4.27 (td, J = 2.8, 10.64 Hz, 1 H), 4.35-4.43 (m, 1H), 6.89-6.92 (m, 1 H), 7.24-7.28 (m, 1 H), 7.31-7.35 (m, 2 H), 7.38 (d, J = 1.8 Hz, 2 H). |

TABLE 4-continued

| Compound No. | Structural formula | 1H-NMR (400MHz) • (ppm) |
|---|---|---|
| 23 | (structure with N-methylpyrazole) | 2.27-2.43 (m, 2 H), 2.50-2.57 (m, 1 H), 2.57-2.66 (m, 1 H), 3.30- 3.33 (m, 1 H), 3.51-3.60 (m, 1H), 3.95 (s, 3 H), 4.26-4.32 (m, 1 H), 4.33-4.40 (m, 1 H), 6.93 (d, J = 8.5 Hz, 1 H), 7.49 (dd, J = 2.1, 8.5Hz, 1 H), 7.54 (d, J = 2.1H, 1 H), 7.82 (s, 1 H), 7.98 (s, 1 H). |

Example 7

Synthesis of 6-(2-fluoropyridin-3-yl)-2,3,5',6'-tetrahydrospiro[chromene-4,4'-[1,3]thiazin]-2'-amine (Compound 24)

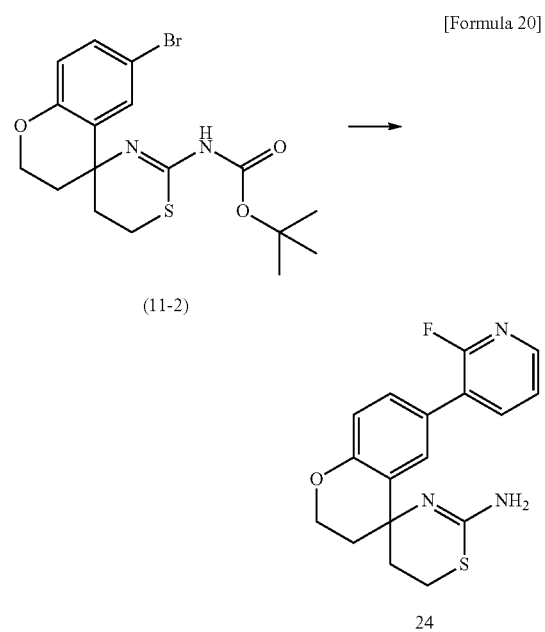

2-Fluoropyridine-3-boronic acid (14.9 mg) was added to a solution of the compound 11-2 (26.3 mg) in N,N-dimethylformaldehyde (0.95 ml). Subsequently, a 1 M sodium bicarbonate solution (0.14 ml) and palladium-triphenyl phosphine (7.8 mg) were added and the mixture was stirred in a nitrogen atmosphere at 100° C. for 12 hours. After confirming disappearance of the raw material, water was added to the reaction mixture. The aqueous layer was extracted with ethyl acetate, and the organic layer was washed with brine. The organic layer was dried over anhydrous magnesium sulfate, and the solvent was evaporated under reduced pressure. The resulting crude product was purified by silica gel column chromatography to obtain the title compound (13.0 mg).

¹H NMR (400 MHz, CDCl₃) (ppm): 2.04-2.18 (m, 2H), 2.29-2.37 (m, 1H), 2.46 (ddd, J=4.0, 10.7, 14.4 Hz, 1H), 3.18-3.24 (m, 2H), 4.31 (dt, J=2.8, 11.4 Hz, 1H), 4.44-4.47

(m, 1H), 6.95 (d, J=8.6 Hz, 1H), 7.24-7.26 (m, 1H), 7.36-7.42 (m, 2H), 7.88 (ddd, J=1.7, 7.6, 9.9 Hz, 1H), 8.15 (dt, J=1.7, 4.6 Hz, 1H).

Example 8

Synthesis of 7-fluoro-6-(2-fluoropyridin-3-yl)-2,3,5',6'-tetrahydrospiro[chromene-4,4'-[1,3]thiazin]-2'-amine (Compound 26)

[Formula 21]

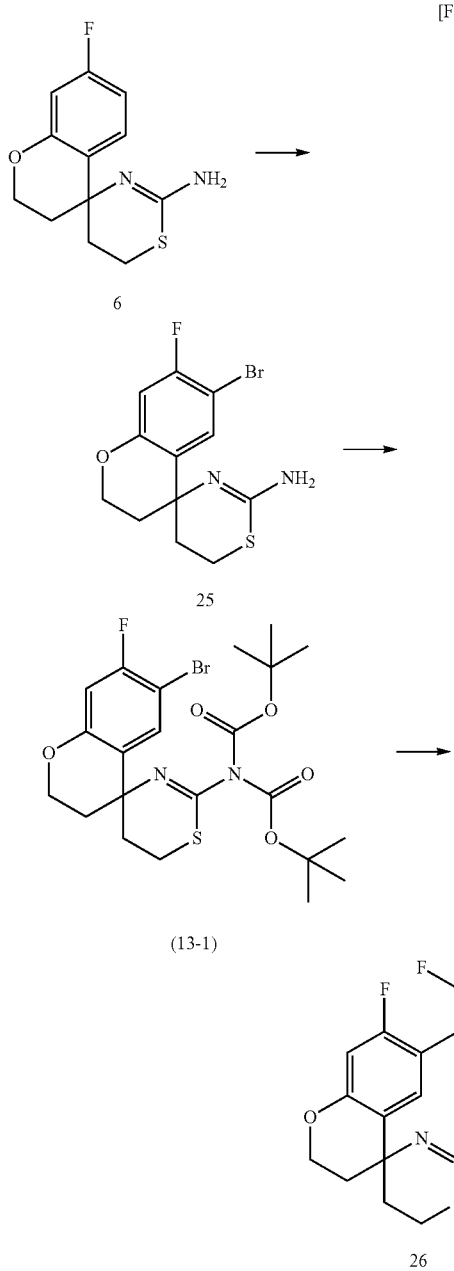

(1) Synthesis of 6-bromo-7-fluoro-2,3,5',6'-tetrahydrospiro[chromene-4,4'-[1,3]thiazin]-2'-amine (Compound 25)

Bromine (12.7 mg) was added to a solution of the compound 6 (20 mg) in acetic acid (1.0 ml) at room temperature, followed by stirring for 30 minutes. After confirming disappearance of the raw material, the reaction mixture was neutralized by adding it to aqueous sodium bicarbonate. The aqueous layer was extracted with ethyl acetate, and the organic layer was washed with brine. The organic layer was dried over anhydrous magnesium sulfate, and the solvent was evaporated under reduced pressure. The resulting crude product 25 (14.4 mg) was used for the next reaction without further purification.

1H NMR (400 MHz, CDCl₃) (ppm): 1.87-1.99 (m, 2H), 1.99-2.28 (m, 2H), 2.97-3.08 (m, 1H), 3.08-3.17 (m, 1H), 4.16-4.28 (m, 1H), 4.30-4.39 (m, 1H), 6.62 (d, J=9.7 Hz, 1H), 7.29 (d, J=7.8 Hz, 1H).

(2) Synthesis of Compound 26

The compound 25 (14.4 mg) was dissolved in methylene chloride (3.0 ml), and di-t-butyl dicarbonate (47.5 mg) was added. Then, N,N-dimethylaminopyridine (26.5 mg) was added and the mixture was stirred at room temperature for six hours. After confirming disappearance of the raw material, the reaction mixture was added to a saturated ammonium chloride solution. The aqueous layer was extracted with methylene chloride, and the organic layer was dried over anhydrous magnesium sulfate. The solvent was evaporated under reduced pressure. The resulting crude product 13-1 (17 mg) was used for the next reaction without further purification.

2-Fluoropyridine-3-boronic acid (7.2 mg) was added to a solution of the crude product 13-1 obtained in the above reaction (17 mg) in N,N-dimethylformaldehyde (0.5 ml). Subsequently, a 1 M sodium bicarbonate solution (0.05 ml) and palladium-triphenyl phosphine (3.8 mg) were added and the mixture was stirred in a nitrogen atmosphere at 100° C. overnight. After confirming disappearance of the raw material, water was added to the reaction mixture. The aqueous layer was extracted with ethyl acetate, and the organic layer was washed with brine. The organic layer was dried over anhydrous magnesium sulfate, and the solvent was evaporated under reduced pressure. The resulting crude product was purified by silica gel column chromatography to obtain the title compound (1.7 mg).

1H NMR (400 MHz, CDCl₃) (ppm): 2.00-2.18 (m, 2H), 2.26-2.51 (m, 2H), 3.14-3.25 (m, 2H), 4.27-4.36 (m, 1H), 4.42-4.48 (m, 1H), 6.70 (d, J=11.1 Hz, 1H), 7.22 (d, J=9.1 Hz, 1H), 7.25-7.34 (m, 1H), 7.86-7.92 (m, 1H), 8.21 (brd, J=4.9 Hz, 1H).

Example 9

Synthesis of 6-[(2-aminopyridin-3-yl)ethynyl]-2,3,5',6'-tetrahydrospiro[chromene-4,4'-[1,3]thiazin]-2'-amine (Compound 27)

[Formula 22]

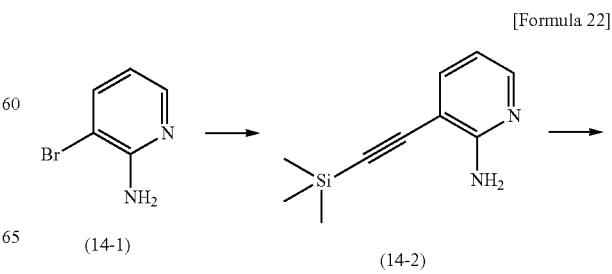

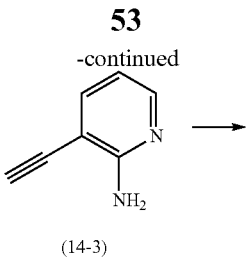

(14-3)

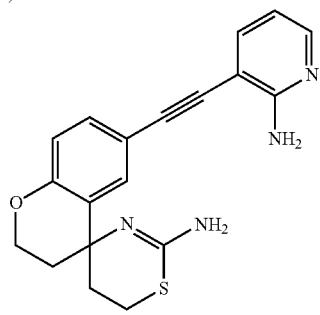

27

(1) Synthesis of 3-[(trimethylsilyl)ethynyl]pyridin-2-amine (Compound 14-2)

The compound 14-1 (200 mg) was dissolved in a mixed solvent of tetrahydrofuran (1.2 ml) and triethylamine (7 ml). Ethynyl(trimethyl)silane (227 mg), copper (I) iodide (8.8 mg) and dichloropalladium-triphenyl phosphine (32.5 mg) were added and the mixture was sealed in a tube. After stirring the mixture at 90° C. for 22 hours, the reaction mixture was added to water to terminate the reaction. The aqueous layer was extracted with ethyl acetate, and the organic layer was washed with brine. The organic layer was dried over anhydrous magnesium sulfate, and the solvent was evaporated under reduced pressure. The resulting crude product was purified by silica gel column chromatography to obtain the title compound (244 mg).

1H NMR (400 MHz, $CDCl_3$) (ppm): 0.26 (s, 9H), 5.08 (br. s., 2H), 6.62 (br. s., 1H), 7.54 d, J=7.2 Hz, 1H), 8.05 (br. s., 1H).

(2) Synthesis of 3-ethynylpyridin-2-amine (Compound 14-3)

The compound 14-2 (244 mg) was dissolved in methanol (15.0 ml). Potassium carbonate (212.6 mg) was added and the mixture was stirred at room temperature for two hours. The reaction mixture was added to water. The aqueous layer was extracted with ethyl acetate, and the organic layer was washed with brine. The organic layer was dried over anhydrous magnesium sulfate, and the solvent was evaporated under reduced pressure. The resulting crude product was purified by silica gel column chromatography to obtain the title compound (93.5 mg).

1H NMR (400 MHz, $CDCl_3$) (ppm): 3.42 (s, 1H), 5.08 (br. s., 2H), 6.63 (dd, J=5.2, 7.4 Hz, 1H), 7.58 (dd, J=7.4, 1.6 Hz, 1H), 8.08 (br. s., 1H).

(3) Synthesis of Compound 27

The compound 14-3 (30 mg) and the compound 20 obtained in Example 11-1 (40 mg) were dissolved in a mixed solvent of tetrahydrofuran (2 ml) and triethylamine (2 ml). Copper (I) iodide (1.2 mg) and dichloropalladium-triphenylphosphine (4.5 mg) were added, and the mixture was sealed in a tube and stirred at 90° C. for 22 hours. The reaction mixture was added to water to terminate the reaction. The aqueous layer was extracted with ethyl acetate, and the organic layer was washed with brine. The organic layer was dried over anhydrous magnesium sulfate, and the solvent was evaporated under reduced pressure. The resulting crude product was purified by NH-silica gel column chromatography and NH-silica gel TLC to obtain the title compound (12.5 mg).

ESI-MS; m/z 351 [M$^+$+H]

1H NMR (400 MHz, $CDCl_3$) (ppm): 1.92-2.12 (m, 3H), 2.25 (ddd, J=4.0, 10.5, 14.2 Hz, 1H), 3.02-3.10 (m, 1H), 3.11-3.20 (m, 1H), 4.26 (td, J=2.9, 11.2 Hz, 1H), 4.38 (dt, J=4.6, 11.2 Hz, 1H), 5.05 (br. s., 2H), 6.63 (dd, J=5.0, 7.5 Hz, 1H), 6.81 (d, J=8.4 Hz, 1H), 7.29 (dd, J=2.0, 8.4 Hz, 1H), 7.34 (d, J=2.0 Hz, 1H), 7.57 (dd, J=1.6, 7.5 Hz, 1H), 7.97-8.05 (m, 1H).

Example 10

Synthesis of 2,3,5',6'-tetrahydrospiro[1,3-thiazine-4,4'-thiochromen]-2-amine (Compound 28)

[Formula 23]

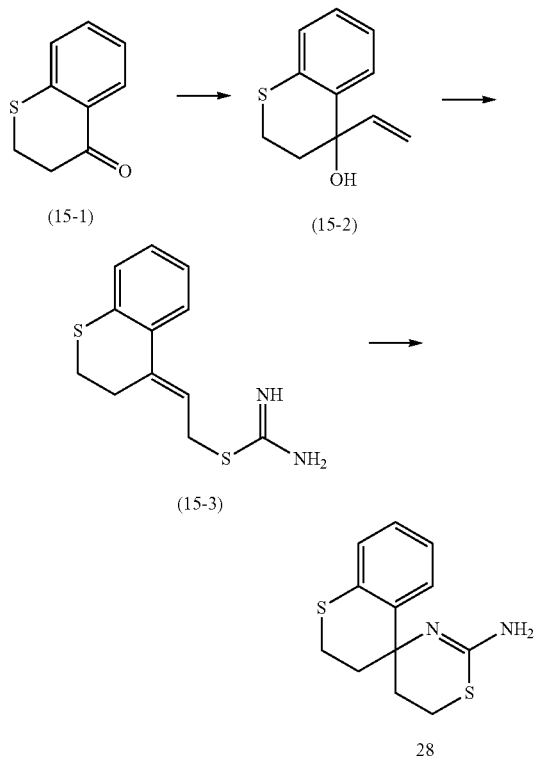

(1) Synthesis of (2E)-2-(2,3-dihydro-4H-thiochromen-4-ylidene)ethyl carbamimidothioate (Compound 15-3)

Zinc chloride (46.1 mg) was added to vinylmagnesium chloride (1.6 M solution in tetrahydrofuran; 2.75 ml), and the mixture was stirred at room temperature for one hour. The mixture was cooled to 0° C., and a solution of the compound 15-1 (555 mg) in tetrahydrofuran (2.0 ml) was added dropwise. The mixture was stirred at the same temperature for five hours. After confirming disappearance of the raw material, an ammonium chloride solution was added to the reaction mixture to terminate the reaction. The aqueous layer was extracted with ethyl acetate, and the organic layer was washed with brine. The organic layer was dried over anhydrous magnesium sulfate, and the solvent was evaporated under reduced pressure to obtain the crude product (665 mg). The crude product was dissolved in acetic acid (5.0 ml), and then thiourea (334 mg) was added. After stirring at room temperature overnight, the insoluble matter was removed by filtration through cotton plug and the filtrate was added dropwise to diethyl ether. The mixture was cooled to 0° C. and stirred. The solid was removed by a glass filter, and the solvent in the filtrate was evaporated under reduced pressure. Ethyl acetate was added to the residual oil, followed by neutralization with aqueous sodium bicarbonate. The aqueous layer was extracted with ethyl acetate, and the organic layer was washed with brine. The organic layer was dried over anhydrous magnesium sulfate. The solid was generated during evaporation of the solvent under reduced pressure. The concentration was stopped and a mixed solvent of hexane and diethyl ether was added. The generated solid was collected by a Kiriyama funnel and washed with diethyl ether. The resulting solid was dried to obtain the title compound (66.5 mg).

$^1$H NMR (400 MHz, MeOD) (ppm): 2.96-3.01 (m, 2H), 3.05-3.10 (m, 2H), 4.08 (d, J=8.0 Hz, 2H), 6.09 (t, J=8.0 Hz, 1H), 7.07-7.20 (m, 3H), 7.50 (dd, J=1.3, 7.9 Hz, 1H).

(2) Synthesis of Compound 28

The compound 15-3 (50 mg) was dissolved in trifluoroacetic acid (0.46 ml), and then trifluoromethanesulfonic acid (0.1 ml) was added thereto in an ice bath. The mixture was stirred at the same temperature for 0.5 hour and then stirred at room temperature for 3.0 hours. After confirming disappearance of the raw material, the reaction mixture was neutralized by adding it to aqueous sodium bicarbonate cooled in an ice bath. The aqueous layer was extracted with ethyl acetate, and the organic layer was washed with brine. The organic layer was dried over anhydrous sodium sulfate, and the solvent was evaporated under reduced pressure. The residue was purified by NH-silica gel column chromatography and then by silica gel TLC to obtain the title compound (1.6 mg).

ESI-MS; m/z 251 [M$^+$+H]

1H NMR (400 MHz, CDCl$_3$) (ppm): 1.87-1.95 (m, 1H), 2.24-2.35 (m, 3H), 2.92-2.98 (m, 2H), 3.07-3.13 (m, 1H), 3.14-3.24 (m, 1H), 7.07-7.12 (m, 1H), 7.13-7.15 (m, 2H), 7.19 (brd, J=1.3 Hz, 1H).

Test Example 1

Quantification of Aβ Peptide in Culture of Neurons from Rat Fetus Brain (1) Rat Primary Neuronal Culture Primary neuronal cultures were prepared from the cerebral cortex of embryonic day 18 Wistar rats (Charles River Japan, Yokohama, Japan). Specifically, the embryos were aseptically removed from pregnant rats under ether anesthesia. The brain was isolated from the embryo and immersed in an ice-cold L-15 medium (such as Invitrogen Corp. Cat #11415-064, Carlsbad, Calif., USA, or SIGMA L1518). The cerebral cortex was collected from the isolated brain under a stereoscopic microscope. The cerebral cortex fragments collected were enzymatically treated in an enzyme solution containing 0.25% trypsin (Invitrogen Corp. Cat #15050-065, Carlsbad, Calif., USA) and 0.01% DNase (Sigma D5025, St. Louis, Mo., USA) at 37° C. for 30 minutes to disperse the cells. Here, the enzymatic reaction was stopped by adding inactivated horse serum to the solution. The enzymatically treated solution was centrifuged at 1,500 rpm for five minutes to remove the supernatant. 5 to 10 ml of a medium was added to the resulting cell mass. Neurobasal medium (Invitrogen Corp. Cat #21103-049, Carlsbad, Calif., USA) supplemented with 2% B27 supplement (Invitrogen Corp. Cat #17504-044, Carlsbad, Calif., USA), 25 μM 2-mercaptoethanol (2-ME, WAKO Cat #139-06861, Osaka, Japan), 0.5 mM L-glutamine (Invitrogen Corp. Cat #25030-081, Carlsbad, Calif., USA), and Antibiotics-Antimycotics (Invitrogen Corp. Cat #15240-062, Carlsbad, Calif., USA) was used as the medium (Neurobasal/B27/2-ME). However, the above Neurobasal medium not supplemented with 2-ME (Neurobasal/B27) was used for the assay. The cells were redispersed by mild pipetting of the cell mass to which the medium was added. The cell dispersion was filtered through a 40-μm nylon mesh (Cell Strainer, Cat #35-2340, Becton Dickinson Labware, Franklin Lakes, N.J., USA) to remove the remaining cell mass, and thus a neuronal cell suspension was obtained. The neuronal cell suspension was diluted with the medium and then plated in a volume of 100 μl/well at an initial cell density of $5 \times 10^5$ cells/cm$^2$ in a 96-well polystyrene culture plate pre-coated with poly-L or D-lysine (Falcon Cat #35-3075, Becton Dickinson Labware, Franklin Lakes, N.J., USA coated with poly-L-lysine using the method shown below, or BIOCOAT™ cell environments Poly-D-lysine cell ware 96-well plate, Cat #35-6461, Becton Dickinson Labware, Franklin Lakes, N.J., USA). Poly-L-lysine coating was carried out as follows. 100 μg/ml of a poly-L-lysine (SIGMA P2636, St. Louis, Mo., USA) solution was aseptically prepared with a 0.15 M borate buffer (pH 8.5). 100 μg/well of the solution was added to the 96-well polystyrene culture plate and incubated at room temperature for one or more hours or at 4° C. overnight or longer. Thereafter, the coated 96-well polystyrene culture plate was washed with sterile water four or more times, and then dried or rinsed with, for example, sterile PBS or medium, and used for cell plating. The plated cells were cultured in the incubator at 37° C. in 5% CO$_2$-95% air for one day. Then, the total amount of the medium was replaced with a fresh Neurobasal/B27/2-ME medium, and then the cells were cultured for further three days.

(2) Addition of Compound

The drug was added to the culture plate on Day 4 of culture as follows. The total amount of the medium was removed from the wells, and 180 μl/well of Neurobasal medium not containing 2-ME and containing 2% B-27 (Neurobasal/B27) was added thereto. A solution of the test compound in dimethyl sulfoxide (hereinafter abbreviated as DMSO) was diluted with Neurobasal/B27 to a concentration 10-fold higher than the final concentration. 20 μl/well of the dilution was added to and sufficiently mixed with the medium. The final DMSO concentration was 1% or less. Only DMSO was added to the control group.

(3) Sampling

The cells were cultured for three days after addition of the compound, and the total amount of the medium was collected. The resulting medium was used as an ELISA sample. The sample was not diluted for ELISA measurement of Aβx-42 and diluted to 5-fold with a diluent supplied with an ELISA kit for ELISA measurement of Aβx-40.

(4) Evaluation of Cell Survival

Cell survival was evaluated by an MTT assay according to the following procedure. After collecting the medium, 100 μl/well of a pre-warmed medium was added to the wells. Further, 8 μl/well of a solution of 8 mg/ml of MTT (SIGMA M2128, St. Louis, Mo., USA) in D-PBS(−) (Dulbecco's phosphate buffered Saline, SIGMA D8537, St. Louis, Mo., USA) was added to the wells. The 96-well polystyrene culture plate was incubated in an incubator at 37° C. in 5% $CO_2$-95% air for 20 minutes. 100 μl/well of an MTT lysis buffer was added thereto, and MTT formazan crystals were sufficiently dissolved in the buffer in the incubator at 37° C. in 5% $CO_2$-95% air. Then, the absorbance at 550 nm in each well was measured. The MTT lysis buffer was prepared as follows. 100 g of SDS (sodium dodecyl sulfate (sodium lauryl sulfate), WAKO 191-07145, Osaka, Japan) was dissolved in a mixed solution of 250 mL of N,N-dimethylformamide (WAKO 045-02916, Osaka, Japan) with 250 mL of distilled water. 350 μl each of concentrated hydrochloric acid and acetic acid were further added to the solution to allow the solution to have a final pH of about 4.7.

Upon measurement, wells having no cells plated and containing only the medium and MTT solution were set as background (bkg). The measured values were respectively applied to the following formula including subtracting bkg values from them. Thus, the proportion against the control group (group not treated with the drug, CTRL) (% of CTRL) was calculated to compare and evaluate cell survival activities.

% of CTRL=($A550\_sample$−$A550\_bkg$)/($A550\_CTRL$−bkg)×100

(A550_sample: absorbance at 550 nm of sample well, A550_bkg: absorbance at 550 nm of background well, A550_CTRL: absorbance at 550 nm of control group well)

(5) Aβ ELISA

Human/Rat β Amyloid (42) ELISA Kit Wako (#290-62601) and Human/Rat β Amyloid (40) ELISA Kit Wako (#294-62501) from Wako Pure Chemical Industries, Ltd. were used for Aβ ELISA. Aβ ELISA was carried out according to the protocols recommended by the manufacturers (methods described in the attached documents). However, the Aβ calibration curve was created using beta-amyloid peptide 1-42, rat and beta-amyloid peptide 1-40, rat (Calbiochem, #171596 [$Aβ_2$], #171593 [$Aβ_{40}$]). The results are shown in Table 5 as IC50 values (μM) for decrease in the Aβ42 concentration in the medium.

TABLE 5

| Compound No. | Aβ42 production reducing effect (μM) |
|---|---|
| 11 | 0.053 |
| 12 | 0.071 |
| 15 | 0.063 |
| 16 | 0.027 |
| 18 | 0.047 |

As is clear from the results of Table 5, the compound of the present invention was proved to have an Aβ42 production reducing effect.

INDUSTRIAL APPLICABILITY

The compound of the general formula (I) or pharmaceutically acceptable salt thereof according to the present invention have an Aβ42 production reducing effect. Thus, the present invention can particularly provide a prophylactic or therapeutic agent for a neurodegenerative disease caused by Aβ such as Alzheimer-type dementia or Down's syndrome.

The invention claimed is:
1. A compound represented by the formula (I):

[Formula 1]

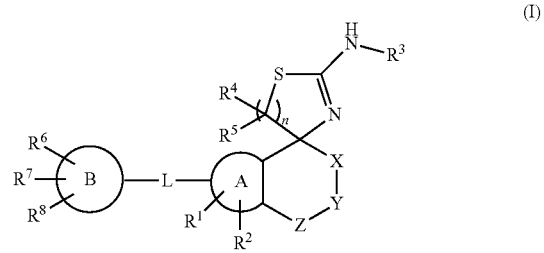

or a pharmaceutically acceptable salt thereof, wherein
Ring A is a C6-10 aryl group or a 5- to 10-membered heterocyclic group,
L is a single bond, an oxygen atom or a group represented by the formula —C(=O)$NR^L$— (wherein $R^L$ is a hydrogen atom or a C1-6 alkyl group which may have 1 to 3 substituents selected from Substituent Group a) or a C1-6 alkylene group, a C2-6 alkenylene group or a C2-6 alkynylene group which may have 1 to 3 substituents selected from Substituent Group α, respectively,
Ring B is a C3-8 cycloalkyl group, a C6-10 aryl group or a 5- to 10-membered heterocyclic group,
X is a C1-3 alkylene group or a C2-3 alkenylene group which may have 1 to 3 substituents selected from Substituent Group α, respectively,
Y is an oxygen atom, a sulfur atom, a sulfoxide group, a sulfone group or a group represented by the formula —$NR^Y$— (wherein $R^Y$ is a hydrogen atom or a C1-6 alkyl group, a C1-6 alkylcarbonyl group, a C3-8 cycloalkylcarbonyl group, a C6-10 arylcarbonyl group, a C1-6 alkylsulfonyl group, a C6-10 arylsulfonyl group, a C6-10 aryl group or a 5- to 6-membered heteroaryl group which may have 1 to 3 substituents selected from Substituent Group α, respectively),
Z is a single bond or a C1-3 alkylene group,
$R^1$ and $R^2$ are each independently a hydrogen atom, a halogen atom, a hydroxy group or a cyano group, or a C1-6 alkyl group or a C1-6 alkoxy group which may have 1 to 3 substituents selected from Substituent Group α, respectively,
$R^3$ is a hydrogen atom or a C1-6 alkyl group, a C1-6 alkylcarbonyl group, a C6-10 arylcarbonyl group, a C1-6 alkylsulfonyl group, a C6-10 arylsulfonyl group, a C3-8 cycloalkyl group, a C6-10 aryl group or a 5- to 10-membered heterocyclic group which may have 1 to 3 substituents selected from Substituent Group α, respectively,
$R^4$ and $R^5$ are each independently a hydrogen atom, a halogen atom or a hydroxy group, or a C1-6 alkyl group, a C1-6 alkoxy group, a C3-8 cycloalkyl group, a C3-8 cycloalkyloxy group, a C6-10 aryl group or a 5- to 10-membered heterocyclic group which may have 1 to 3 substituents selected from Substituent Group α, respectively,
$R^6$, $R^7$ and $R^8$ are each independently a hydrogen atom, a halogen atom, a hydroxy group or a cyano group, or a C1-6 alkyl group, a C2-6 alkenyl group, a C2-6 alkynyl group, a C1-6 alkoxy group, a C3-8 cycloalkyl group, a C3-8 cycloalkyloxy group, a C6-10 aryl group or a 5- to 10-membered heterocyclic group which may have 1 to 3 substituents selected from Substituent Group α, respectively, and n is an integer of 1 to 3

[Substituent Group α: a hydrogen atom, a halogen atom, a hydroxy group, an oxo group, a cyano group, a C1-6 alkyl group, a trifluoromethyl group, a trifluoromethoxy group, a C1-6 alkoxy group, a C3-8 cycloalkyl group, a C3-8 cycloalkyloxy group, a C6-10 aryl group and a 5- to 10-membered heterocyclic group].

2. The compound or pharmaceutically acceptable salt thereof according to claim 1, wherein X is a C1-3 alkylene group which may have 1 to 3 substituents selected from Substituent Group α.

3. The compound or pharmaceutically acceptable salt thereof according to claim 1, wherein Y is an oxygen atom.

4. The compound or pharmaceutically acceptable salt thereof according to claim 1, wherein Y is a sulfur atom or a sulfone group.

5. The compound or pharmaceutically acceptable salt thereof according to claim 1, wherein Y is a group represented by the formula —NR$^Y$— (wherein R$^Y$ is a hydrogen atom or a C1-6 alkyl group, a C1-6 alkylcarbonyl group, a C3-8 cycloalkylcarbonyl group, a C6-10 arylcarbonyl group, a C1-6 alkylsulfonyl group, a C6-10 arylsulfonyl group, a C6-10 aryl group or a 5- to 6-membered heteroaryl group which may have 1 to 3 substituents selected from Substituent Group α, respectively).

6. The compound or pharmaceutically acceptable salt thereof according to claim 1, wherein L is a group represented by the formula —C(=O)NR$^L$— (wherein R$^L$ is a hydrogen atom or a C1-6 alkyl group which may have 1 to 3 substituents selected from Substituent Group α).

7. A compound selected from the following compounds:
1) (−)-N-(2'-amino-2,3,5',6'-tetrahydro spiro[chromene-4,4'-[1,3]thiazin]-6-yl)-5-cyanopyridine-2-carboxamide,
2) N-(2'-amino-2,3,5',6'-tetrahydro spiro[chromene-4,4'-[1,3]thiazin]-6-yl)-5-trifluoromethylpyridine-2-carboxamide,
3) N-(2'-amino-2,3,5',6'-tetrahydrospiro[chromene-4,4'-[1,3]thiazin]-6-yl)-3,5-difluoropyridine-2-carboxamide,
4) N-(2'-amino-2,3,5',6'-tetrahydro spiro[chromene-4,4'-[1,3]thiazin]-6-yl)-5-bromopyrimidine-2-carboxamide,
5) N-(2'-amino-2,3,5',6'-tetrahydro spiro[chromene-4,4'-[1,3]thiazin]-6-yl)-5-bromopyrimidine-2-carboxamide or
6) N-(2'-amino-2,3,5',6'-tetrahydro spiro[chromene-4,4'-[1,3]thiazin]-6-yl)-3,5-dichloropyridine-2-carboxamide, or a pharmaceutically acceptable salt thereof.

8. A pharmaceutical composition comprising the compound or pharmaceutically acceptable salt thereof according to claim 1 as an active ingredient.

9. A pharmaceutical composition comprising the compound or pharmaceutically acceptable salt thereof according to claim 7 as an active ingredient.

10. A method of treating Down's syndrome, comprising administering an effective amount of the pharmaceutical composition according to claim 8 to a subject in need thereof.

11. A method of treating Alzheimer-type dementia, comprising administering an effective amount of the pharmaceutical composition according to claim 8 to a subject in need thereof.

12. A method of treating Down's syndrome, comprising administering an effective amount of the pharmaceutical composition according to claim 9 to a subject in need thereof.

13. A method of treating Alzheimer-type dementia, comprising administering an effective amount of the pharmaceutical composition according to claim 9 to a subject in need thereof.

* * * * *

UNITED STATES PATENT AND TRADEMARK OFFICE
CERTIFICATE OF CORRECTION

| | | |
|---|---|---|
| PATENT NO. | : 8,501,733 B2 | Page 1 of 1 |
| APPLICATION NO. | : 13/055830 | |
| DATED | : August 6, 2013 | |
| INVENTOR(S) | : Takafumi Motoki et al. | |

It is certified that error appears in the above-identified patent and that said Letters Patent is hereby corrected as shown below:

In the Claims

Column 58
Line 26, replace "Substituent Group a)" with --Substituent Group α)--.

Column 59
Line 36, replace "tetrahydro spiro" with --tetrahydrospiro--.

Column 60
Line 1, replace "tetrahydro spiro" with --tetrahydrospiro--.

Column 60
Line 7, replace "tetrahydro spiro" with --tetrahydrospiro--.

Column 60
Line 9, replace "tetrahydro spiro" with --tetrahydrospiro--.

Column 60
Line 10, after "carboxamide" insert --,--.

Column 60
Line 12, replace "tetrahydro spiro" with --tetrahydrospiro--.

Signed and Sealed this
Twenty-eighth Day of January, 2014

Michelle K. Lee
*Deputy Director of the United States Patent and Trademark Office*